United States Patent
Ozaki et al.

(10) Patent No.: US 9,381,285 B2
(45) Date of Patent: Jul. 5, 2016

(54) CENTRIFUGAL PUMP APPARATUS

(75) Inventors: Takayoshi Ozaki, Iwata (JP); Hiroyuki Yamada, Iwata (JP); Kenichi Suzuki, Iwata (JP); Ken Sugiura, Iwata (JP)

(73) Assignee: THORATEC CORPORATION, Pleasanton, CA (US)

( * ) Notice: Subject to any disclaimer, the term of this patent is extended or adjusted under 35 U.S.C. 154(b) by 897 days.

(21) Appl. No.: 13/254,597

(22) PCT Filed: Feb. 26, 2010

(86) PCT No.: PCT/JP2010/053069
§ 371 (c)(1), (2), (4) Date: Sep. 2, 2011

(87) PCT Pub. No.: WO2010/101082
PCT Pub. Date: Sep. 10, 2010

(65) Prior Publication Data
US 2012/0003108 A1 Jan. 5, 2012

(30) Foreign Application Priority Data
Mar. 5, 2009 (JP) ................. 2009-052176

(51) Int. Cl.
*F04D 29/00* (2006.01)
*A61M 1/10* (2006.01)
(Continued)

(52) U.S. Cl.
CPC ............ *A61M 1/1017* (2014.02); *A61M 1/101* (2013.01); *A61M 1/1015* (2014.02);
(Continued)

(58) Field of Classification Search
CPC .............. A61M 1/1017; A61M 1/1015; F04D 13/0666; F04D 29/0473; F04D 29/048; F04D 29/2261; F16C 17/045; F16C 32/0692
USPC ................ 417/420, 423.12, 423.14; 604/151; 384/123
See application file for complete search history.

(56) References Cited

U.S. PATENT DOCUMENTS

| 1,093,868 A | 4/1914 | Leighty |
| 2,684,035 A | 7/1954 | Kemp |

(Continued)

FOREIGN PATENT DOCUMENTS

| CN | 102239334 A | 11/2011 |
| CN | 102341600 A | 2/2012 |

(Continued)

OTHER PUBLICATIONS

Extended European Search Report issued in European Patent Application No. EP 10748677.1 dated Nov. 19, 2012.
(Continued)

*Primary Examiner* — Bryan Lettman
*Assistant Examiner* — Christopher Bobish
(74) *Attorney, Agent, or Firm* — Kilpatrick Townsend & Stockton LLP

(57) ABSTRACT

A centrifugal blood pump apparatus includes an impeller provided in a blood chamber, first and second permanent magnets provided in one surface and the other surface of the impeller respectively, a third permanent magnet provided in an inner wall of the blood chamber, and a magnetic element and a coil for driving the impeller to rotate with a diaphragm being interposed. First and second grooves for hydrodynamic bearing different in shape and depth from each other are formed in the inner wall of the blood chamber facing the impeller, and third and fourth grooves for hydrodynamic bearing different in shape and depth from each other are formed in the diaphragm facing the impeller. The second and fourth grooves for hydrodynamic bearing generate high hydrodynamic pressure when the impeller is activated to rotate, while the first and third grooves for hydrodynamic bearing generate high hydrodynamic pressure when the impeller steadily rotates.

11 Claims, 22 Drawing Sheets

(51) Int. Cl.
  *F16C 17/04* (2006.01)
  *F16C 32/06* (2006.01)
  *F04D 13/06* (2006.01)
  *F04D 29/048* (2006.01)
  *F04D 29/22* (2006.01)
  *F04D 29/42* (2006.01)
  *F04D 29/047* (2006.01)

(52) U.S. Cl.
  CPC ......... *F04D 13/0666* (2013.01); *F04D 29/048* (2013.01); *F04D 29/0473* (2013.01); *F04D 29/2261* (2013.01); *F04D 29/426* (2013.01); *F16C 17/045* (2013.01); *F16C 32/0692* (2013.01)

(56) References Cited

U.S. PATENT DOCUMENTS

| | | | |
|---|---|---|---|
| 3,510,229 A | 5/1970 | Smith | |
| 3,870,382 A * | 3/1975 | Reinhoudt | 384/123 |
| 3,932,069 A | 1/1976 | Giardini et al. | |
| 3,960,468 A | 6/1976 | Boorse et al. | |
| 4,149,535 A | 4/1979 | Voider | |
| 4,382,199 A | 5/1983 | Isaacson | |
| 4,392,836 A | 7/1983 | Sugawara | |
| 4,507,048 A | 3/1985 | Belenger et al. | |
| 4,540,402 A | 9/1985 | Aigner | |
| 4,549,860 A | 10/1985 | Yakich | |
| 4,686,982 A | 8/1987 | Nash | |
| 4,688,998 A | 8/1987 | Olsen et al. | |
| 4,753,221 A | 6/1988 | Kensey et al. | |
| 4,769,006 A | 9/1988 | Papantonakos | |
| 4,790,843 A | 12/1988 | Carpentier et al. | |
| 4,806,080 A | 2/1989 | Mizobuchi et al. | |
| 4,817,586 A | 4/1989 | Wampler | |
| 4,846,152 A | 7/1989 | Wampler et al. | |
| 4,895,557 A | 1/1990 | Moise et al. | |
| 4,900,227 A | 2/1990 | Troup lin | |
| 4,902,272 A | 2/1990 | Milder et al. | |
| 4,906,229 A | 3/1990 | Wampler | |
| 4,908,012 A | 3/1990 | Moise et al. | |
| 4,919,647 A | 4/1990 | Nash | |
| 4,930,997 A | 6/1990 | Bennett | |
| 4,944,722 A | 7/1990 | Carriker et al. | |
| 4,957,504 A | 9/1990 | Chardack | |
| 4,969,865 A | 11/1990 | Hwang et al. | |
| 4,985,014 A | 1/1991 | Orejola | |
| 4,995,857 A | 2/1991 | Arnold | |
| 5,092,844 A | 3/1992 | Schwartz et al. | |
| 5,092,879 A | 3/1992 | Jarvik | |
| 5,106,263 A | 4/1992 | Irie | |
| 5,106,273 A | 4/1992 | Lemarquand et al. | |
| 5,106,372 A | 4/1992 | Ranford | |
| 5,112,202 A | 5/1992 | Oshima et al. | |
| 5,112,349 A | 5/1992 | Summers et al. | |
| 5,129,883 A | 7/1992 | Black | |
| 5,145,333 A | 9/1992 | Smith | |
| 5,147,186 A | 9/1992 | Buckholtz | |
| 5,190,528 A | 3/1993 | Fonger et al. | |
| 5,201,679 A | 4/1993 | Velte et al. | |
| 5,211,546 A | 5/1993 | Isaacson et al. | |
| 5,275,580 A | 1/1994 | Yamazaki | |
| 5,290,227 A | 3/1994 | Pasque | |
| 5,290,236 A | 3/1994 | Mathewson | |
| 5,306,295 A | 4/1994 | Kolff et al. | |
| 5,312,341 A | 5/1994 | Turi | |
| 5,332,374 A | 7/1994 | Kricker et al. | |
| 5,346,458 A | 9/1994 | Afield | |
| 5,350,283 A | 9/1994 | Nakazeki et al. | |
| 5,354,331 A | 10/1994 | Schachar | |
| 5,360,445 A | 11/1994 | Goldowsky | |
| 5,370,509 A | 12/1994 | Golding et al. | |
| 5,385,581 A | 1/1995 | Bramm et al. | |
| 5,405,383 A | 4/1995 | Barr | |
| 5,449,342 A | 9/1995 | Hirose et al. | |
| 5,478,222 A | 12/1995 | Heidelberg et al. | |
| 5,504,978 A | 4/1996 | Meyer, III | |
| 5,507,629 A | 4/1996 | Jarvik | |
| 5,533,957 A | 7/1996 | Aldea | |
| 5,569,111 A | 10/1996 | Cho et al. | |
| 5,575,630 A | 11/1996 | Nakazawa et al. | |
| 5,595,762 A | 1/1997 | Derrieu et al. | |
| 5,611,679 A | 3/1997 | Ghosh et al. | |
| 5,613,935 A | 3/1997 | Jarvik | |
| 5,643,226 A | 7/1997 | Cosgrove et al. | |
| 5,678,306 A | 10/1997 | Bozeman, Jr. et al. | |
| 5,692,882 A | 12/1997 | Bozeman, Jr. et al. | |
| 5,695,471 A | 12/1997 | Wampler | |
| 5,725,357 A | 3/1998 | Nakazeki et al. | |
| 5,738,649 A | 4/1998 | Macoviak | |
| 5,746,575 A | 5/1998 | Westphal et al. | |
| 5,746,709 A | 5/1998 | Rom et al. | |
| 5,749,855 A | 5/1998 | Reitan | |
| 5,755,784 A | 5/1998 | Jarvik | |
| 5,776,111 A | 7/1998 | Tesio | |
| 5,795,074 A * | 8/1998 | Rahman et al. | 384/123 |
| 5,800,559 A | 9/1998 | Higham et al. | |
| 5,807,311 A | 9/1998 | Palestrant | |
| 5,814,011 A | 9/1998 | Corace | |
| 5,824,069 A | 10/1998 | Lemole | |
| 5,851,174 A | 12/1998 | Jarvik et al. | |
| 5,853,394 A | 12/1998 | Tolkoff et al. | |
| 5,868,702 A | 2/1999 | Stevens et al. | |
| 5,868,703 A | 2/1999 | Bertolero et al. | |
| 5,890,883 A | 4/1999 | Golding et al. | |
| 5,924,848 A | 7/1999 | Izraelev | |
| 5,924,975 A | 7/1999 | Goldowsky | |
| 5,928,131 A | 7/1999 | Prem | |
| 5,938,412 A | 8/1999 | Israelev | |
| 5,941,813 A | 8/1999 | Sievers et al. | |
| 5,947,703 A | 9/1999 | Nojiri et al. | |
| 5,951,263 A | 9/1999 | Taylor et al. | |
| 5,964,694 A | 10/1999 | Siess et al. | |
| 6,004,269 A | 12/1999 | Crowley et al. | |
| 6,007,479 A | 12/1999 | Rottenberg et al. | |
| 6,030,188 A | 2/2000 | Nojiri et al. | |
| 6,042,347 A | 3/2000 | Scholl et al. | |
| 6,053,705 A | 4/2000 | Schob et al. | |
| 6,058,593 A | 5/2000 | Siess | |
| 6,066,086 A | 5/2000 | Antaki et al. | |
| 6,071,093 A | 6/2000 | Hart | |
| 6,074,180 A | 6/2000 | Khanwilkar et al. | |
| 6,080,133 A | 6/2000 | Wampler | |
| 6,082,900 A | 7/2000 | Takeuchi et al. | |
| 6,086,527 A | 7/2000 | Talpade | |
| 6,100,618 A | 8/2000 | Schoeb et al. | |
| 6,123,659 A | 9/2000 | leBlanc et al. | |
| 6,123,726 A | 9/2000 | Mori et al. | |
| 6,139,487 A | 10/2000 | Siess | |
| 6,142,752 A | 11/2000 | Akamatsu et al. | |
| 6,143,025 A | 11/2000 | Stobie et al. | |
| 6,146,325 A | 11/2000 | Lewis et al. | |
| 6,149,683 A | 11/2000 | Lancisi et al. | |
| 6,158,984 A | 12/2000 | Cao et al. | |
| 6,171,078 B1 | 1/2001 | Schob | |
| 6,176,822 B1 | 1/2001 | Nix et al. | |
| 6,176,848 B1 | 1/2001 | Rau et al. | |
| 6,190,304 B1 | 2/2001 | Downey et al. | |
| 6,206,659 B1 | 3/2001 | Izraelev | |
| 6,227,797 B1 | 5/2001 | Watterson et al. | |
| 6,227,820 B1 | 5/2001 | Jarvik | |
| 6,234,772 B1 | 5/2001 | Wampler et al. | |
| 6,234,998 B1 | 5/2001 | Wampler | |
| 6,245,007 B1 | 6/2001 | Bedingham et al. | |
| 6,247,892 B1 | 6/2001 | Kazatchkov et al. | |
| 6,254,359 B1 | 7/2001 | Aber | |
| 6,264,635 B1 | 7/2001 | Wampler et al. | |
| 6,276,831 B1 * | 8/2001 | Takahashi et al. | 384/100 |
| 6,293,901 B1 | 9/2001 | Prem | |
| 6,295,877 B1 | 10/2001 | Aboul-Hosn et al. | |
| 6,319,231 B1 | 11/2001 | Andrulitis | |
| 6,351,048 B1 | 2/2002 | Schob et al. | |
| 6,375,607 B1 | 4/2002 | Prem | |
| 6,422,990 B1 | 7/2002 | Prem | |

(56) References Cited

U.S. PATENT DOCUMENTS

| | | | |
|---|---|---|---|
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |
| 6,458,163 B1 | 10/2002 | Slemker et al. |
| 6,508,777 B1 | 1/2003 | Macoviak et al. |
| 6,508,787 B2 | 1/2003 | Erbel et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 | 4/2003 | Ozaki et al. |
| 6,595,762 B2 | 7/2003 | Khanwilkar et al. |
| 6,609,883 B2 | 8/2003 | Woodard et al. |
| 6,623,420 B2 | 9/2003 | Reich et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,189 B1 | 4/2004 | Jarvik et al. |
| 6,776,578 B2 | 8/2004 | Belady |
| 6,790,171 B1 | 9/2004 | Griindeman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,860,713 B2 | 3/2005 | Hoover |
| 6,926,662 B1 | 8/2005 | Aboul-Hosn et al. |
| 6,935,344 B1 | 8/2005 | Aboul-Hosn et al. |
| 6,942,672 B2 | 9/2005 | Heilman et al. |
| 6,949,066 B2 | 9/2005 | Bearnson et al. |
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,027,875 B2 | 4/2006 | Siess et al. |
| 7,048,681 B2 | 5/2006 | Tsubouchi et al. |
| 7,090,401 B2 * | 8/2006 | Rahman et al. ............. 384/114 |
| 7,112,903 B1 | 9/2006 | Schob |
| 7,128,538 B2 | 10/2006 | Tsubouchi et al. |
| 7,156,802 B2 | 1/2007 | Woodard et al. |
| 7,160,243 B2 | 1/2007 | Medvedev |
| 7,172,551 B2 | 2/2007 | Leasure |
| 7,175,588 B2 | 2/2007 | Morello |
| 7,241,257 B1 | 7/2007 | Ainsworth et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,431,688 B2 | 10/2008 | Wampler et al. |
| 7,467,930 B2 | 12/2008 | Ozaki et al. |
| 7,470,246 B2 | 12/2008 | Mori et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,699,586 B2 | 4/2010 | LaRose et al. |
| 7,731,675 B2 | 6/2010 | Aboul-Hosn et al. |
| 7,748,964 B2 | 7/2010 | Yaegashi et al. |
| 7,802,966 B2 | 9/2010 | Wampler et al. |
| 7,841,976 B2 | 11/2010 | McBride et al. |
| 7,888,242 B2 | 2/2011 | Tanaka et al. |
| 7,934,909 B2 | 5/2011 | Nuesser et al. |
| 7,976,271 B2 | 7/2011 | LaRose et al. |
| 7,997,854 B2 | 8/2011 | LaRose et al. |
| 8,007,254 B2 | 8/2011 | LaRose et al. |
| 8,096,935 B2 | 1/2012 | Sutton et al. |
| 8,123,669 B2 | 2/2012 | Siess et al. |
| 8,226,373 B2 | 7/2012 | Yaehashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Akdis et al. |
| 8,585,290 B2 * | 11/2013 | Bauer ............. 384/107 |
| 2002/0058994 A1 | 5/2002 | Hill et al. |
| 2002/0095210 A1 | 7/2002 | Finnegan et al. |
| 2003/0023302 A1 | 1/2003 | Moe et al. |
| 2004/0007515 A1 | 1/2004 | Geyer |
| 2004/0024285 A1 | 2/2004 | Muckter |
| 2004/0030381 A1 | 2/2004 | Shu |
| 2004/0210305 A1 | 10/2004 | Shu et al. |
| 2005/0089422 A1 | 4/2005 | Ozaki et al. |
| 2005/0287022 A1 | 12/2005 | Yaehashi et al. |
| 2006/0024182 A1 | 2/2006 | Akdis et al. |
| 2006/0055274 A1 | 3/2006 | Kim |
| 2007/0078293 A1 | 4/2007 | Shambaugh, Jr. |
| 2007/0134993 A1 | 6/2007 | Tamez et al. |
| 2007/0189648 A1 * | 8/2007 | Kita et al. ............. 384/123 |
| 2007/0213690 A1 | 9/2007 | Phillips et al. |
| 2007/0231135 A1 | 10/2007 | Wampler et al. |
| 2007/0297923 A1 * | 12/2007 | Tada ............. 417/356 |
| 2008/0021394 A1 | 1/2008 | La Rose et al. |
| 2008/0030895 A1 | 2/2008 | Obara et al. |
| 2008/0124231 A1 | 5/2008 | Yaegashi |
| 2009/0060743 A1 | 3/2009 | McBride et al. |
| 2009/0074336 A1 | 3/2009 | Engesser et al. |
| 2009/0171136 A1 | 7/2009 | Shambaugh, Jr. |
| 2009/0257693 A1 * | 10/2009 | Aiello ............. 384/123 |
| 2011/0118766 A1 | 5/2011 | Reichenbach et al. |
| 2011/0118829 A1 | 5/2011 | Hoarau et al. |
| 2011/0129373 A1 | 6/2011 | Mori |
| 2011/0243759 A1 | 10/2011 | Ozaki et al. |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0035411 A1 | 2/2012 | LaRose et al. |
| 2012/0078030 A1 | 3/2012 | Bourque |
| 2012/0130152 A1 | 5/2012 | Ozaki et al. |
| 2012/0243759 A1 | 9/2012 | Fujisawa |
| 2012/0308363 A1 | 12/2012 | Ozaki et al. |
| 2013/0121821 A1 | 5/2013 | Ozaki et al. |
| 2013/0170970 A1 | 7/2013 | Ozaki et al. |
| 2013/0178694 A1 | 7/2013 | Jeffery et al. |
| 2013/0243623 A1 | 9/2013 | Okawa et al. |
| 2014/0030122 A1 | 1/2014 | Ozaki et al. |
| 2015/0017030 A1 | 1/2015 | Ozaki |

FOREIGN PATENT DOCUMENTS

| | | |
|---|---|---|
| EP | 1113117 A2 | 7/2001 |
| EP | 1495773 A2 | 1/2005 |
| EP | 1495773 A3 | 11/2006 |
| EP | 1495773 B1 | 2/2009 |
| EP | 2372160 A1 | 10/2011 |
| EP | 2405140 A1 | 1/2012 |
| EP | 2461465 A1 | 6/2012 |
| JP | 58/9535 | 1/1983 |
| JP | 61/293146 | 12/1986 |
| JP | 04-091396 | 3/1992 |
| JP | 04/148094 A | 5/1992 |
| JP | 05/021197 U | 3/1993 |
| JP | 06/014538 U | 2/1994 |
| JP | 6-53790 | 7/1994 |
| JP | 2006/070476 | 9/1994 |
| JP | 2006/245455 | 9/1994 |
| JP | 07/014220 U | 3/1995 |
| JP | 07/042869 U | 8/1995 |
| JP | 07/509156 A | 10/1995 |
| JP | 09/122228 A | 5/1997 |
| JP | 10/331641 A | 12/1998 |
| JP | 11/244377 A | 9/1999 |
| JP | 2001/039628 | 11/2001 |
| JP | 2003/135592 A | 5/2003 |
| JP | 2004/166401 A | 6/2004 |
| JP | 2004-209240 | 7/2004 |
| JP | 2004/332566 A | 11/2004 |
| JP | 2004/346925 A | 12/2004 |
| JP | 2005/094955 | 4/2005 |
| JP | 2005/127222 A | 5/2005 |
| JP | 2005/245138 | 9/2005 |
| JP | 2005/270345 A | 10/2005 |

(56) References Cited

FOREIGN PATENT DOCUMENTS

| | | | |
|---|---|---|---|
| JP | 2005/270415 A | 10/2005 | |
| JP | 2005/287599 A | 10/2005 | |
| JP | 2006-167173 | 6/2006 | |
| JP | 2007/002885 A | 1/2007 | |
| JP | 2007/043821 | 2/2007 | |
| JP | 2007-089972 | 4/2007 | |
| JP | 2007-089974 | 4/2007 | |
| JP | 2007/215292 | 8/2007 | |
| JP | 2007/247489 | 9/2007 | |
| JP | 2008/011611 | 1/2008 | |
| JP | 2008/104278 | 5/2008 | |
| JP | 2008/132131 | 6/2008 | |
| JP | 2008/99453 | 8/2008 | |
| JP | 2008/193838 | 8/2008 | |
| JP | 2008/297997 A | 12/2008 | |
| JP | 2008/301634 | 12/2008 | |
| JP | 2006/254619 | 9/2009 | |
| JP | 2010/136863 A | 6/2010 | |
| JP | 2012/021413 | 2/2012 | |
| WO | WO-93/07388 A1 | 4/1993 | |
| WO | 96/31934 | 10/1996 | |
| WO | 97/42413 A1 | 11/1997 | |
| WO | WO-2005/028000 A1 | 3/2005 | |
| WO | 2005/034312 A2 | 4/2005 | |
| WO | 2009/157408 | 12/2009 | |
| WO | 2010/067682 A1 | 6/2010 | |
| WO | 2010/101082 A1 | 9/2010 | |
| WO | 2011/013483 A1 | 2/2011 | |

OTHER PUBLICATIONS

Asama, et al., "Suspension Performance of a Two-Axis Actively Regulated Consequent-Pole Bearingless Motor," IEEE Transactions on Energy Conversion, vol. 28, No. 4, Dec. 2013, 8 pages.

European Search report Issued in European Patent Application No. 10/748,702.7, mailed Apr. 2, 2013.

International Search Report (PCT/ISA/210) issued on Jul. 14, 2009, by Japanese Patent Office as the International Searching Authority for International Application No. PCT/JP2009/061318.

International Search Report and Written Opinion issued in PCT/JP2011/050925, mailed Apr. 12, 2011.

International Search Report and Written Opinion issued in PCT/JP2011/054134, mailed Apr. 12, 2011.

International Search Report and Written Opinion issued in PCT/JP2011/064768, mailed Sep. 13, 2011.

International Search Report and Written Opinion issued in PCT/JP2011/070450, mailed Dec. 13, 2011.

Kosaka, et al.,"Operating Point Control System for a Continuous Flow Artificial Heart: In Vitro Study," ASAIO Journal 2003, 6 pages.

Supplementary European Search Report issued in European Application No. 09/831,788.6, dated Jan. 7, 2013, 7 pages.

Terumo Heart, Inc., "Handled With Care—Significantly Reduce the Risk of Cell Damage," Terumo brochure, Apr. 2010, 2 pages.

Yamazaki, et al., "Development of a Miniature Intraventricular Axial Flow Blood Pump," ASAIO Journal, 1993, 7 pages.

International Search Report and Written Opinion of PCT/US2014/012448 mailed on Feb. 19, 2014.

Extended European Search Report in EP Application No. 11806627.3 mailed on Oct. 8, 2014, 8 pages.

* cited by examiner

DEGREE(deg)

HYDRODYNAMIC PRESSURE 0          2/3     1
W22/WL21
(W24/WL23)

CENTRIFUGAL PUMP APPARATUS

RELATED APPLICATIONS

This application is the U.S. National Phase under 35 U.S.C. §371 of International Application No. PCT/JP2010/053069, filed on Feb. 26, 2010, which in turn claims the benefit of Japanese Application No. 2009-052176, filed on Mar. 5, 2009, the disclosures of which Applications are incorporated by reference herein.

TECHNICAL FIELD

The present invention relates to a centrifugal pump apparatus, and particularly to a centrifugal pump apparatus including an impeller for delivering liquid by centrifugal force during rotation.

BACKGROUND ART

In recent years, a centrifugal blood pump apparatus in which driving torque from an external motor is transmitted to an impeller in a blood chamber through magnetic coupling has increasingly been used as a blood circulation apparatus of an artificial heart-lung machine. According to such a centrifugal blood pump apparatus, physical contact between the blood chamber and the outside can be eliminated, thus preventing invasion of bacteria and the like into blood.

A centrifugal blood pump in PTL 1 (Japanese Patent Laying-Open No. 2004-209240) includes a housing having first to third chambers partitioned from one another by first and second diaphragms, an impeller rotatably provided in the second chamber (blood chamber), a magnetic element provided in one surface of the impeller, an electromagnet provided in the first chamber to face the one surface of the impeller, a permanent magnet provided in the other surface of the impeller, a rotor and a motor provided in the third chamber, and a permanent magnet provided in the rotor to face the other surface of the impeller. A groove for hydrodynamic bearing is formed in a surface of the second diaphragm facing the other surface of the impeller. Owing to attractive force acting on the one surface of the impeller from the electromagnet, attractive force acting on the other surface of the impeller from the permanent magnet in the rotor, and a hydrodynamic bearing effect of the grooves for hydrodynamic bearing, the impeller moves away from an inner surface of the second chamber and rotates without contacting.

A centrifugal blood pump in PTL 2 (Japanese Patent Laying-Open No. 2006-167173) includes a housing having first to third chambers partitioned from one another by first and second diaphragms, an impeller rotatably provided in the second chamber (blood chamber), a magnetic element provided in one surface of the impeller, a first permanent magnet provided in the first chamber to face the one surface of the impeller, a second permanent magnet provided in the other surface of the impeller, a rotor and a motor provided in the third chamber, and a third permanent magnet provided in the rotor to face the other surface of the impeller. A first hydrodynamic hearing is formed in a surface of the first diaphragm facing the one surface of the impeller, and a second groove for hydrodynamic bearing is formed in a surface of the second diaphragm facing the other surface of the impeller. Owing to attractive force acting on the one surface of the impeller from the first permanent magnet, attractive force acting on the other surface of the impeller from the third permanent magnet in the rotor, and a hydrodynamic bearing effect of the first and second grooves for hydrodynamic bearing, the impeller moves away from an inner surface of the second chamber and rotates without contacting.

A turbo-type pump in FIGS. 8 and 9 of PTL 3 (Japanese Patent Laying-Open No. 4-91396) includes a housing, an impeller rotatably provided in the housing, a first permanent magnet provided in one surface of the impeller, a rotor provided outside the housing, a second permanent magnet provided in the rotor to face the one surface of the impeller, a third permanent magnet provided in the other surface of the impeller, and a magnetic element provided in the housing to face the other surface of the impeller. A first groove for hydrodynamic bearing is formed in the one surface of the impeller, and a second groove for hydrodynamic hearing is formed in the other surface of the impeller. Owing to attractive force acting on the one surface of the impeller from the second permanent magnet in the rotor, attractive force acting on the other surface of the impeller from the magnetic element in the housing, and a hydrodynamic bearing effect of the first and second grooves for hydrodynamic bearing, the impeller moves away from an inner surface of the housing and rotates without contacting.

A clean pump in PTL 4 (Japanese Utility Model Laying-Open No. 6-53790) includes a casing, an impeller rotatably provided in the casing, a first permanent magnet provided in one surface of the impeller, a rotor provided outside the casing, a second permanent magnet provided in the rotor to face the one surface of the impeller, a magnetic element provided in the other surface of the impeller, and an electromagnet provided outside a housing to face the other surface of the impeller. A groove for hydrodynamic bearing is formed in the one surface of the impeller.

The electromagnet is actuated when a rotation speed of the impeller is lower than a prescribed rotation speed, and power supply to the electromagnet is stopped when the rotation speed of the impeller becomes higher than the prescribed rotation speed. Owing to attractive force acting on the one surface of the impeller from the second permanent magnet in the rotor and a hydrodynamic bearing effect of the groove for hydrodynamic bearing, the impeller moves away from an inner surface of the housing and rotates without contacting.

CITATION LIST

Patent Literature

PTL 1: Japanese Patent Laying-Open No. 2004-209240
PTL 2: Japanese Patent Laying-Open No. 2006-167173
PTL 3: Japanese Patent Laying-Open No. 4-91396
PTL 4: Japanese Utility Model Laying-Open No. 6-53790

SUMMARY OF INVENTION

Technical Problem

The pumps in PTLs 1 to 4 described above are common in the feature of axially supporting the impeller by the grooves for hydrodynamic bearing formed in a portion where the impeller and the housing face each other and radially supporting the impeller by the attractive force between the permanent magnet provided in the impeller and the permanent magnet provided outside the housing.

Since a hydrodynamic bearing does not actively control a position of an impeller like a magnetically levitated bearing, a position of the impeller is varied depending on a rotation speed of the impeller or viscosity of a liquid. For example, when rotation of the impeller has stopped, a hydrodynamic bearing effect is not produced and hence the impeller is in contact with an inner wall of the housing owing to attractive force between the permanent magnet provided in the impeller and a permanent magnet or the like provided to face the permanent magnet. Therefore, frictional resistance between the impeller and the inner wall of the housing becomes great when the impeller is activated to rotate, which causes damage to the impeller and the inner wall of the housing. Consequently, formation of a thrombus may be induced or hemolysis may occur.

In order to address this, PTL 2 also proposes a method of providing an electromagnet for biasing the impeller toward a prescribed direction and a magnetic force adjustment coil for varying magnetic force of the permanent magnets, and actuating them when the impeller is activated to rotate, to smoothly activate the impeller. This approach, however, requires new dedicated members such as the electromagnet and the coil, which leads to increase in a pump size, and increase in the number of components results in lower reliability. These are serious problems for a blood pump for use in an artificial heart or the like.

In view of the above, a main object of the present invention is to provide a centrifugal pump apparatus capable of smoothly activating an impeller to rotate without increasing the number of components.

Solution to Problem

A centrifugal pump apparatus according to the present invention is a centrifugal pump apparatus including a housing having first and second chambers partitioned from each other by a diaphragm, an impeller rotatably provided in the first chamber along the diaphragm, for delivering liquid by centrifugal force during rotation, and a drive unit provided in the second chamber for driving the impeller to rotate with the diaphragm being interposed, and it includes a first magnetic element provided in one surface of the impeller, a second magnetic element provided in an inner wall of the first chamber facing the one surface of the impeller, for attracting the first magnetic element, and a third magnetic element provided in the other surface of the impeller and attracted by the drive unit. During rotation of the impeller, first attractive force between the first and second magnetic elements and second attractive force between the third magnetic element and the drive unit are balanced with each other substantially in a center of a movable range of the impeller in the first chamber. A plurality of first grooves for hydrodynamic hearing and a plurality of second grooves for hydrodynamic bearing are formed in one surface of the impeller or in the inner wall of the first chamber facing the one surface, and a plurality of third grooves for hydrodynamic bearing and a plurality of fourth grooves for hydrodynamic bearing are formed in the other surface of the impeller or in the diaphragm facing the other surface. At least one of a shape and a depth of the second groove for hydrodynamic bearing is different from that of the first groove for hydrodynamic bearing and at least one of a shape and a depth of the fourth groove for hydrodynamic bearing is different from that of the third groove for hydrodynamic bearing. Therefore, by causing the first and third grooves for hydrodynamic bearing to generate high hydrodynamic pressure when the impeller is located at a position intermediate between the diaphragm and the inner wall of the first chamber and by causing the second and fourth grooves for hydrodynamic bearing to generate high hydrodynamic pressure when the impeller is proximate to the diaphragm or to the inner wall of the first chamber, the impeller can smoothly be activated to rotate without increasing the number of components.

Preferably, the plurality of first grooves for hydrodynamic bearing generate hydrodynamic pressure higher than that generated by the plurality of second grooves for hydrodynamic bearing while the impeller steadily rotates, and the plurality of second grooves for hydrodynamic bearing generate hydrodynamic pressure higher than that generated by the plurality of first grooves for hydrodynamic bearing while the impeller is activated to rotate. The plurality of third grooves for hydrodynamic bearing generate hydrodynamic pressure higher than that generated by the plurality of fourth grooves for hydrodynamic bearing while the impeller steadily rotates, and the plurality of fourth grooves for hydrodynamic bearing generate hydrodynamic pressure higher than that generated by the plurality of third grooves for hydrodynamic bearing while the impeller is activated to rotate.

Further preferably, the second groove for hydrodynamic bearing is shallower than the first groove for hydrodynamic bearing and the fourth groove for hydrodynamic bearing is shallower than the third groove for hydrodynamic bearing.

Further preferably, the second groove for hydrodynamic bearing has a depth not greater than one fifth as great as a depth of the first groove for hydrodynamic bearing and the fourth groove for hydrodynamic bearing has a depth not greater than one fifth as great as a depth of the third groove for hydrodynamic bearing.

Further preferably, each second groove for hydrodynamic bearing is arranged between the two first grooves for hydrodynamic bearing and each fourth groove for hydrodynamic bearing is arranged between the two third grooves for hydrodynamic bearing. Each second groove for hydrodynamic bearing has a width not greater than two thirds as great as an interval between the two first grooves for hydrodynamic bearing and each fourth groove for hydrodynamic bearing has a width not greater than two thirds as great as an interval between the two third grooves for hydrodynamic bearing.

Further preferably, the number of the second grooves for hydrodynamic bearing is equal to or smaller than the number of the first grooves for hydrodynamic bearing and the number of the fourth grooves for hydrodynamic bearing is equal to or smaller than the number of the third grooves for hydrodynamic bearing.

Further preferably, the plurality of second grooves for hydrodynamic bearing are arranged at regular angular intervals in a direction of rotation of the impeller and the plurality of fourth grooves for hydrodynamic bearing are arranged at regular angular intervals in the direction of rotation of the impeller.

Further preferably, a plurality of the third magnetic elements are provided, and the plurality of third magnetic elements are arranged along the same circle such that adjacent magnetic polarities are different from each other. The drive unit includes a plurality of coils provided to face the plurality of third magnetic elements, for generating rotating magnetic field.

Further preferably, a plurality of the third magnetic elements are provided, and the plurality of third magnetic elements are arranged along the same circle such that adjacent magnetic polarities are different from each other. The drive unit includes a plurality of fourth magnetic elements arranged to face the plurality of third magnetic elements and a plurality of coils provided in correspondence with the plurality of fourth magnetic elements respectively and each wound around the corresponding fourth magnetic element, for generating rotating magnetic field.

Further preferably, the drive unit includes a rotor rotatably provided along the diaphragm in the second chamber, a fourth magnetic element provided in the rotor to face the third magnetic element, for attracting the third magnetic element, and a motor for rotating the rotor.

Further preferably, the liquid is blood, and the centrifugal pump apparatus is used for circulating the blood. In this case, the impeller is smoothly activated to rotate and a distance between the impeller and the housing is secured, thereby preventing occurrence of hemolysis.

Advantageous Effects of Invention

As described above, according to the present invention, the impeller can smoothly be activated to rotate without increasing the number of components. Furthermore, hemolysis can be avoided when circulating blood.

DESCRIPTION OF EMBODIMENTS

[First Embodiment]

Figure 1:
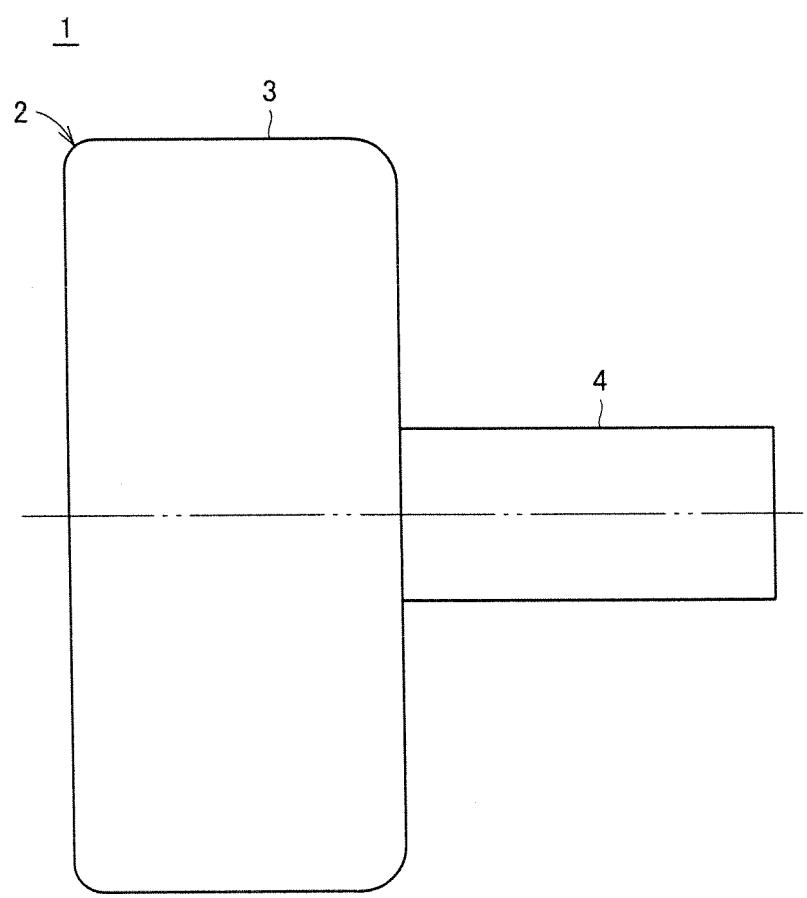
FIG. 1 is a front view showing the appearance of a pump unit of a centrifugal blood pump apparatus according to a first embodiment of the present invention.
Figure 2:
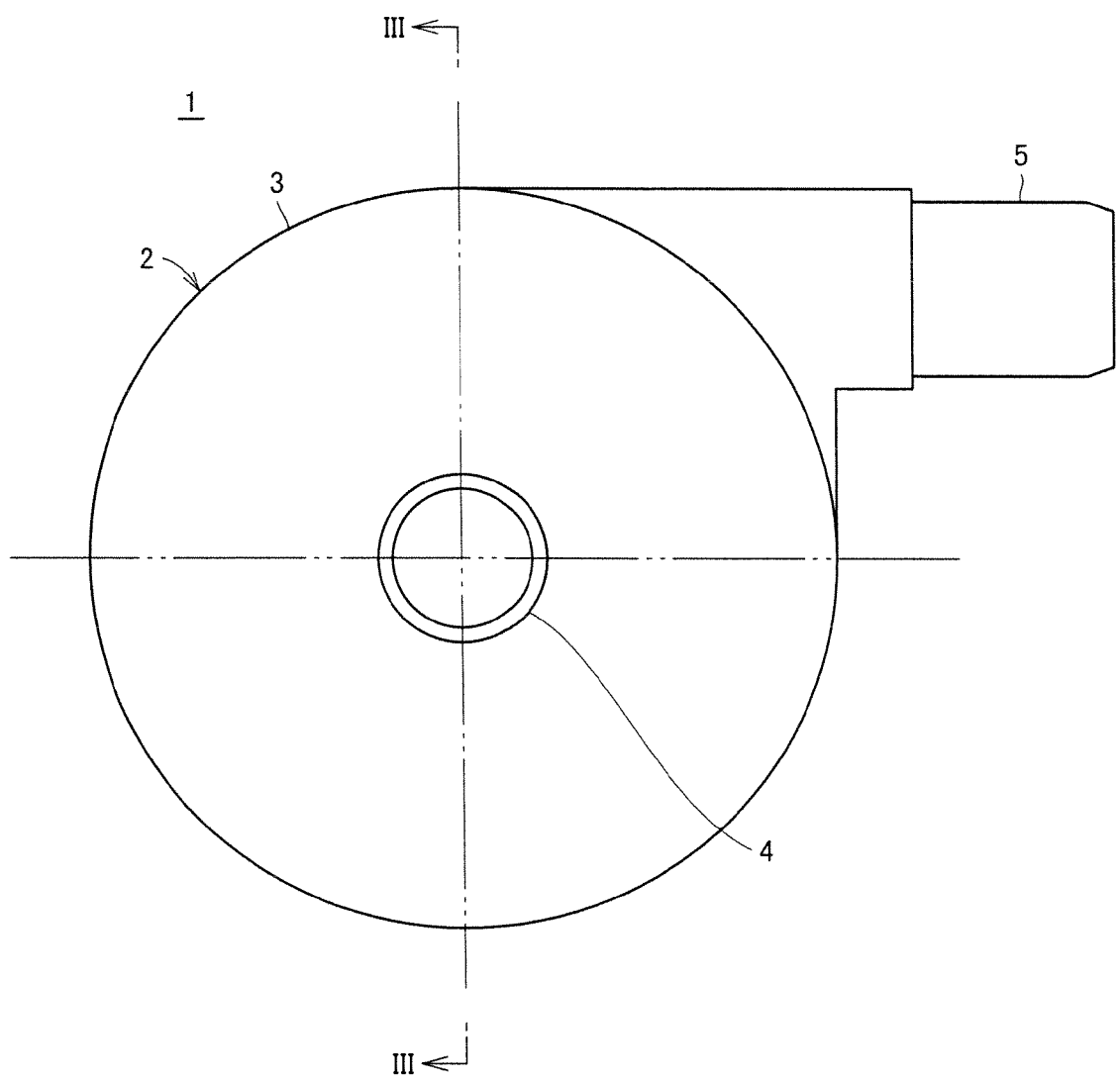
FIG. 2 is a side view of the pump unit shown in FIG. 1.

As shown in FIGS. 1 and 2, a pump unit 1 of a centrifugal blood pump apparatus according to a first embodiment includes a housing 2 made of a nonmagnetic material. Housing 2 includes a cylindrical body portion 3, a cylindrical blood inlet port 4 provided to stand at a center of one end surface of body portion 3, and a cylindrical blood outlet port 5 provided on an outer circumferential surface of body portion 3. Blood outlet port 5 extends in a tangential direction of the outer circumferential surface of body portion 3.

Figure 3:
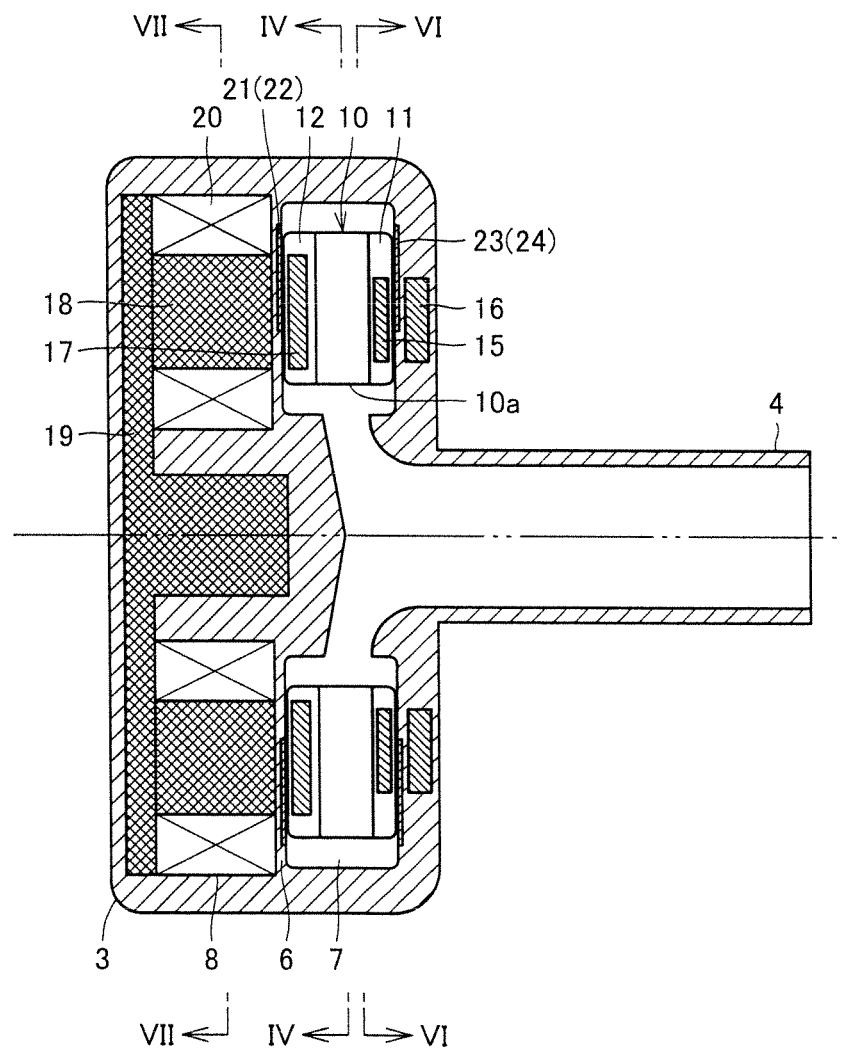
FIG. 3 is a cross-sectional view along the line III-III in FIG. 2.
Figure 4:
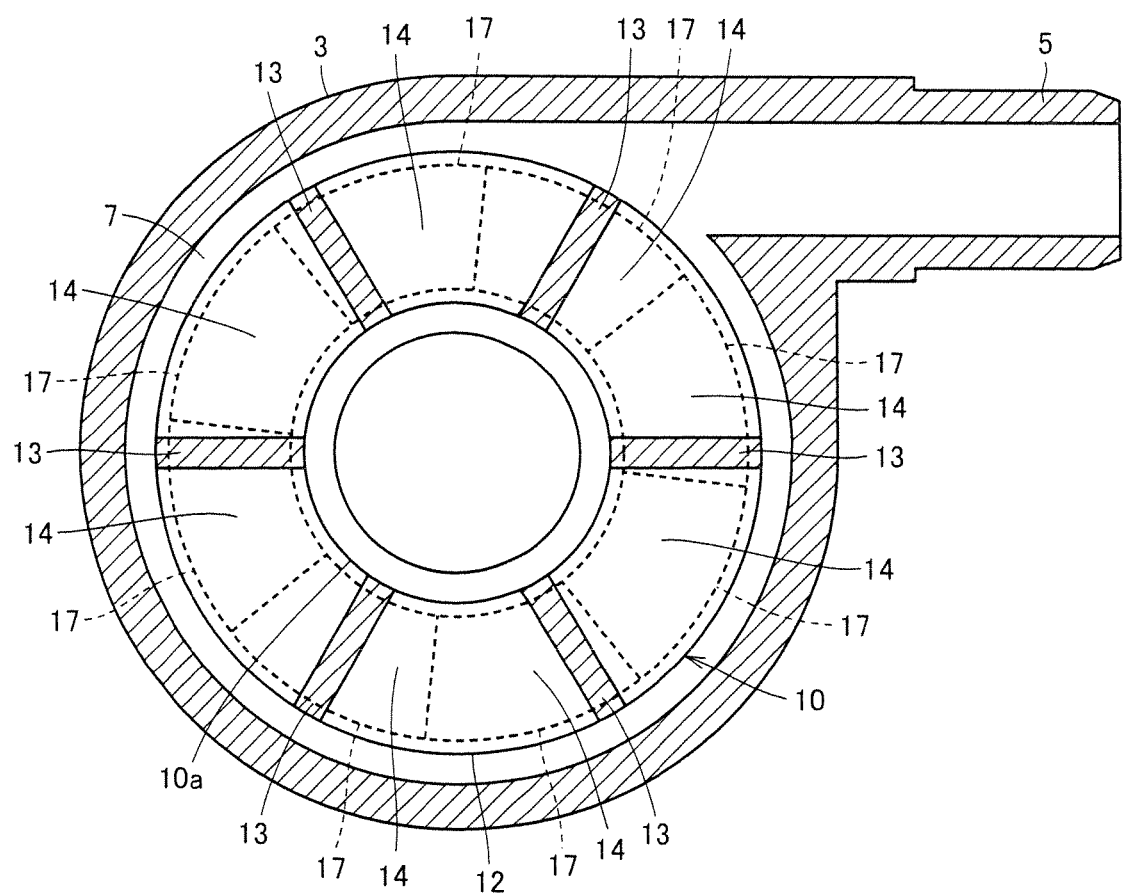
FIG. 4 is a cross-sectional view along the line IV-IV in FIG. 3.

In housing 2, as shown in FIG. 3, a blood chamber 7 and a motor chamber 8 partitioned from each other by a diaphragm 6 are provided. In blood chamber 7, as shown in FIGS. 3 and 4, a disc-shaped impeller 10 having a through hole 10a in a center thereof is rotatably provided. Impeller 10 includes two shrouds 11, 12 in a doughnut plate shape, and a plurality of (e.g., six) vanes 13 formed between two shrouds 11 and 12. Shroud 11 is arranged on the blood inlet port 4 side and shroud 12 is arranged on the diaphragm 6 side. Shrouds 11, 12 and vanes 13 are made of a nonmagnetic material.

A plurality of (six in this case) blood passages 14 partitioned from one another by the plurality of vanes 13 are formed between two shrouds 11 and 12. As shown in FIG. 4, blood passage 14 is in communication with through hole 10a in the center of impeller 10, and it extends with through hole 10a in impeller 10 as a starting point to an outer circumference such that blood passage 14 gradually increases in width. In other words, vane 13 is formed between two adjacent blood passages 14. In the first embodiment, the plurality of vanes 13 are formed at regular angular intervals, and they have the same shape. Thus, the plurality of blood passages 14 are provided at regular angular intervals and they have the same shape.

When impeller 10 is driven to rotate, blood that has flowed in through blood inlet port 4 is delivered by centrifugal force from through hole 10a to an outer circumferential portion of impeller 10 via blood passages 14 and it flows out through blood outlet port 5.

A permanent magnet 15 is embedded in shroud 11 and a permanent magnet 16 for attracting permanent magnet 15 is embedded in an inner wall of blood chamber 7 facing shroud 11. Permanent magnets 15 and 16 are provided to attract (in other words, bias) impeller 10 to the side opposite to motor chamber 8, that is, toward blood inlet port 4.

Instead of providing permanent magnets 15 and 16 in shroud 11 and the inner wall of blood chamber 7, respectively, a permanent magnet may be provided in one of shroud 11 and the inner wall of blood chamber 7, and a magnetic element may be provided in the other. Alternatively, shroud 11 itself may be formed of permanent magnet 15 or a magnetic element. Either a soft magnetic element or a hard magnetic element may be used as the magnetic element.

A single permanent magnet 16 or a plurality of permanent magnets 16 may be provided. If a single permanent magnet 16 is provided, permanent magnet 16 is formed in a ring shape. If a plurality of permanent magnets 16 are provided, the plurality of permanent magnets 16 are arranged at regular angular intervals along the same circle. As with permanent magnet 16, a single permanent magnet 15 or a plurality of permanent magnets 15 may be provided.

As shown in FIGS. 3 and 4, a plurality of (e.g., eight) permanent magnets 17 are embedded in shroud 12. The plurality of permanent magnets 17 are arranged at regular angular intervals along the same circle such that adjacent magnetic polarities thereof are different from each other. In other words, permanent magnet 17 having the N-pole toward motor chamber 8 and permanent magnet 17 having the S-pole toward motor chamber 8 are alternately arranged at regular angular intervals along the same circle.

Figure 7:
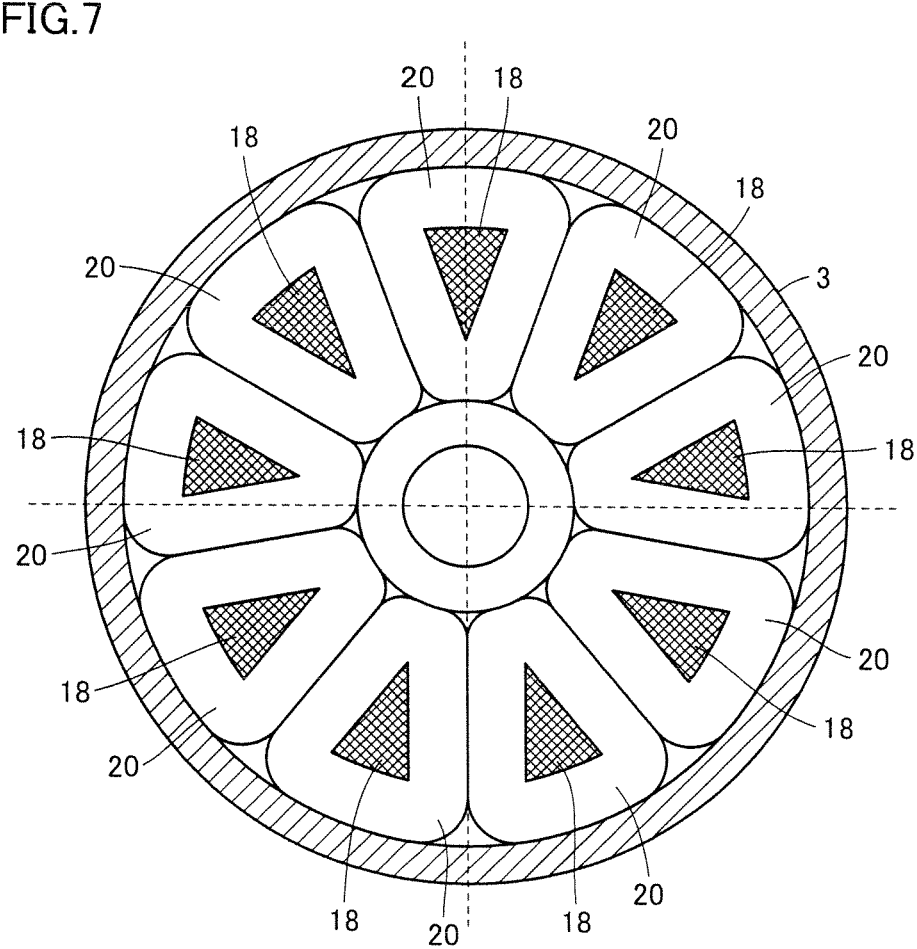
FIG. 7 is a cross-sectional view along the line VII-VII in FIG. 3.

As shown in FIGS. 3 and 7, a plurality of (e.g., nine) magnetic elements 18 are provided in motor chamber 8. The plurality of magnetic elements 18 are arranged at regular angular intervals along the same circle to face the plurality of permanent magnets 17 in impeller 10. A base end of each of the plurality of magnetic elements 18 is joined to one disc-shaped yoke 19. A coil 20 is wound around each magnetic element 18.

Each of the plurality of magnetic elements 18 is formed in a shape of a triangular prism of the same dimensions. In addition, a space for winding coil 20 is equally secured around the plurality of magnetic elements 18, and surfaces facing each other of every two adjacent magnetic elements 18 are provided substantially in parallel to each other. Thus, a large space for coils 20 can be secured and turns of coils 20 can be increased. As a result, large torque for driving impeller 10 to rotate can be generated. Further, copper loss that occurs in coils 20 can be reduced, thereby increasing energy efficiency when impeller 10 is driven to rotate.

An outline surface surrounding the plurality of magnetic elements 18 (a circle surrounding the peripheries of the plurality of magnetic elements 18 in FIG. 7) may correspond to an outline surface surrounding the plurality of permanent magnets 17 (a circle surrounding the peripheries of the plurality of magnetic elements 18 in FIG. 4), or the outline surface surrounding the plurality of magnetic elements 18 may be larger than the outline surface surrounding the plurality of permanent magnets 17. Further, it is preferable that magnetic element 18 be designed not to magnetically be saturated at maximum rating of pump 1 (a condition that torque for driving impeller 10 to rotate becomes maximum).

Figure 8:
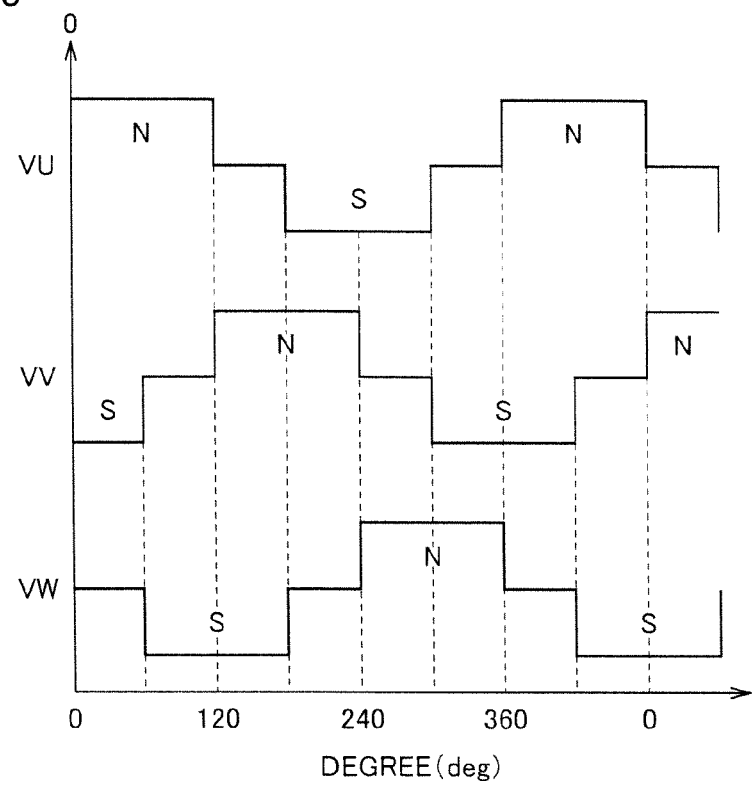
FIG. 8 is a time chart illustrating voltages applied to a plurality of coils shown in FIG. 7.

Voltages are applied to nine coils 20 in a power distribution system shifted by 120 degrees, for example. That is, nine coils 20 are divided into groups each including three coils. Voltages VU, VV and VW as shown in FIG. 8 are applied to first to third coils 20 of each group, respectively. To first coil 20, a positive voltage is applied during a period of 0 to 120 degrees, 0 V is applied during a period of 120 to 180 degrees, a negative voltage is applied during a period of 180 to 300 degrees, and 0 V is applied during a period of 300 to 360 degrees. Accordingly, a tip surface of magnetic element 18 having first coil 20 wound therearound (end surface on the impeller 10 side) becomes the N-pole during the period of 0 to 120 degrees and becomes the S-pole during the period of 180 to 300 degrees. Voltage VV is delayed in phase from voltage VU by 120 degrees, and voltage VW is delayed in phase from voltage VV by 120 degrees. Thus, rotating magnetic field can be formed by applying voltages VU, VV and VW to first to third coils 20, respectively, so that impeller 10 can be rotated by attractive force and repulsion force between the plurality of magnetic elements 18 and the plurality of permanent magnets 17 in impeller 10.

When impeller 10 is rotating at a rated rotation speed, attractive force between permanent magnets 15 and 16 and attractive force between the plurality of permanent magnets 17 and the plurality of magnetic elements 18 are set to be balanced with each other substantially around a center of a movable range of impeller 10 in blood chamber 7. Thus, force acting on impeller 10 due to the attractive force is very small throughout the movable range of impeller 10. Consequently, frictional resistance during relative slide between impeller 10 and housing 2 which occurs when impeller 10 is activated to rotate can be reduced. In addition, a surface of impeller 10 and a surface of an inner wall of housing 2 are not damaged (no projections and recesses in the surfaces) during the relative slide, and moreover, impeller 10 is readily levitated from housing 2 without contacting even when hydrodynamic pressure is small during low-speed rotation. Accordingly, occurrence of hemolysis due to the relative slide between impeller 10 and housing 2 or occurrence of thrombus due to small damage (projections and recesses) to the surfaces which occurs during the relative slide is avoided.

A plurality of grooves for hydrodynamic bearing 21 and a plurality of grooves for hydrodynamic bearing 22 are formed in a surface of diaphragm 6 facing shroud 12 of impeller 10, and a plurality of grooves for hydrodynamic bearing 23 and a plurality of grooves for hydrodynamic bearing 24 are formed in the inner wall of blood chamber 7 facing shroud 11. When a rotation speed of impeller 10 becomes higher than a prescribed rotation speed, a hydrodynamic bearing effect is produced between each of grooves for hydrodynamic bearing 21 to 24 and impeller 10. As a result, drag is generated on impeller 10 from each of grooves for hydrodynamic bearing 21 to 24, causing impeller 10 to rotate without contacting in blood chamber 7.

Figure 5:
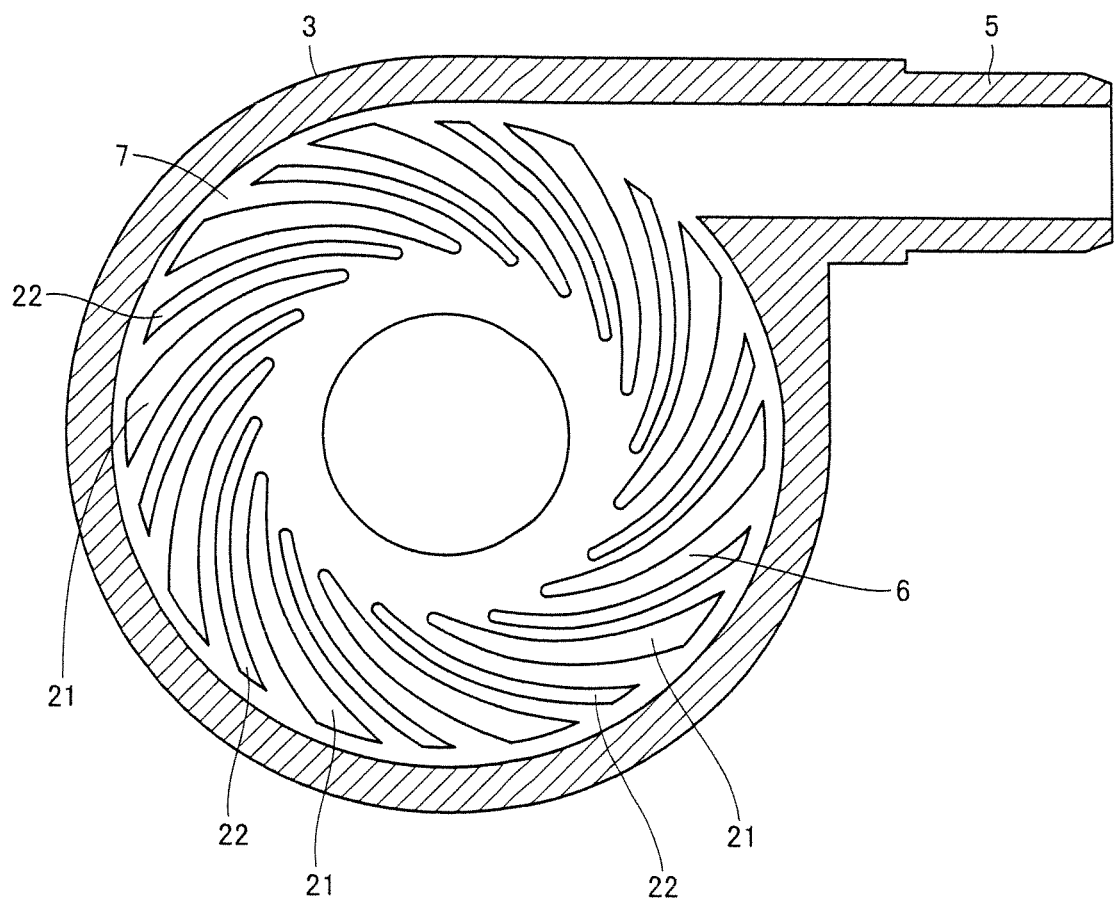
FIG. 5 is a cross-sectional view showing a state where an impeller has been removed from the cross-sectional view along the line IV-IV in FIG. 3.

Specifically, as shown in FIG. 5, the plurality of grooves for hydrodynamic bearing 21 and the plurality of grooves for hydrodynamic bearing 22 are each formed with a size corresponding to shroud 12 of impeller 10. The plurality of grooves for hydrodynamic bearing 21 and the plurality of grooves for hydrodynamic bearing 22 are alternately arranged one by one, in a direction of rotation of impeller 10. Each of grooves for hydrodynamic bearing 21, 22 has one end on an edge (circumference) of a circular portion slightly distant from a center of diaphragm 6, and extends spirally (in other words, in a curved manner) toward a portion near an outer edge of diaphragm 6 such that grooves for hydrodynamic bearing 21, 22 gradually increase in width. The plurality of grooves for hydrodynamic bearing 21 have substantially the same shape, and they are arranged at regular angular intervals in the direction of rotation of impeller 10. Groove for hydrodynamic bearing 21 is a concave portion, and it preferably has a depth of about 0.005 to 0.4 mm. It is preferable that about 6 to 36 grooves for hydrodynamic bearing 21 be provided. The plurality of grooves for hydrodynamic bearing 22 have substantially the same shape, and they are arranged at regular angular intervals in the direction of rotation of impeller 10. Groove for hydrodynamic bearing 22 is a concave portion, and it preferably has a depth of about 0.005 to 0.3 mm.

Figure 9:
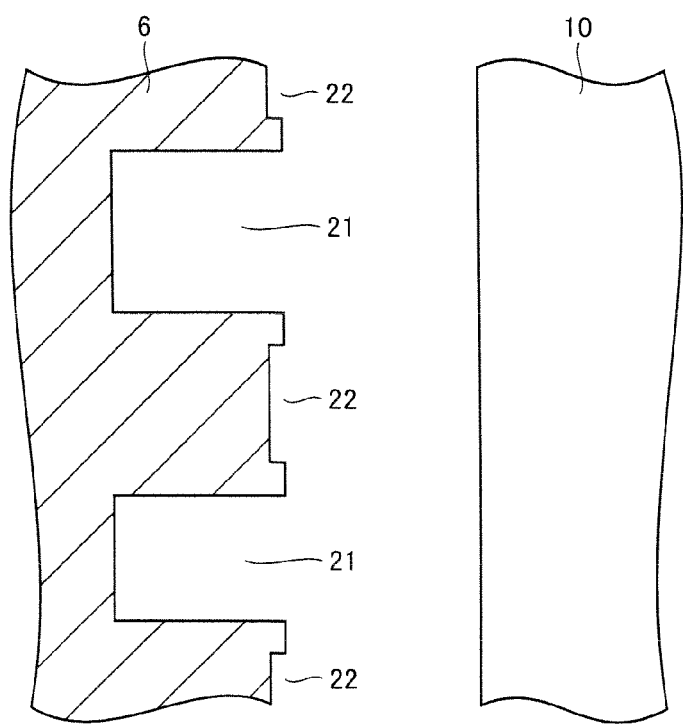
FIG. 9 is a cross-sectional view showing a depth of a groove for hydrodynamic bearing 21, 22 shown in FIG. 5.

As shown in FIG. 9, groove for hydrodynamic bearing 22 is shallower than groove for hydrodynamic bearing 21. Groove for hydrodynamic bearing 22 has a depth preferably not greater than one fifth as great as a depth of groove for hydrodynamic bearing 22. In addition, groove for hydrodynamic bearing 22 has a width preferably not greater than two thirds as great as an interval between two grooves for hydrodynamic bearing 21. Further, the number of grooves for hydrodynamic bearing 22 is preferably equal to or smaller than the number of grooves for hydrodynamic bearing 21.

In FIG. 5, ten grooves for hydrodynamic bearing 21 and ten grooves for hydrodynamic bearing 22 are arranged at regular angular intervals with respect to a central axis of impeller 10. Since each of grooves for hydrodynamic bearing 21, 22 has a so-called inward spiral groove shape, clockwise rotation of impeller 10 causes increase in liquid pressure from an outer diameter portion toward an inner diameter portion of grooves for hydrodynamic bearing 21, 22. As a result, repulsion force is generated between impeller 10 and diaphragm 6 and it acts as hydrodynamic pressure.

Figure 10:
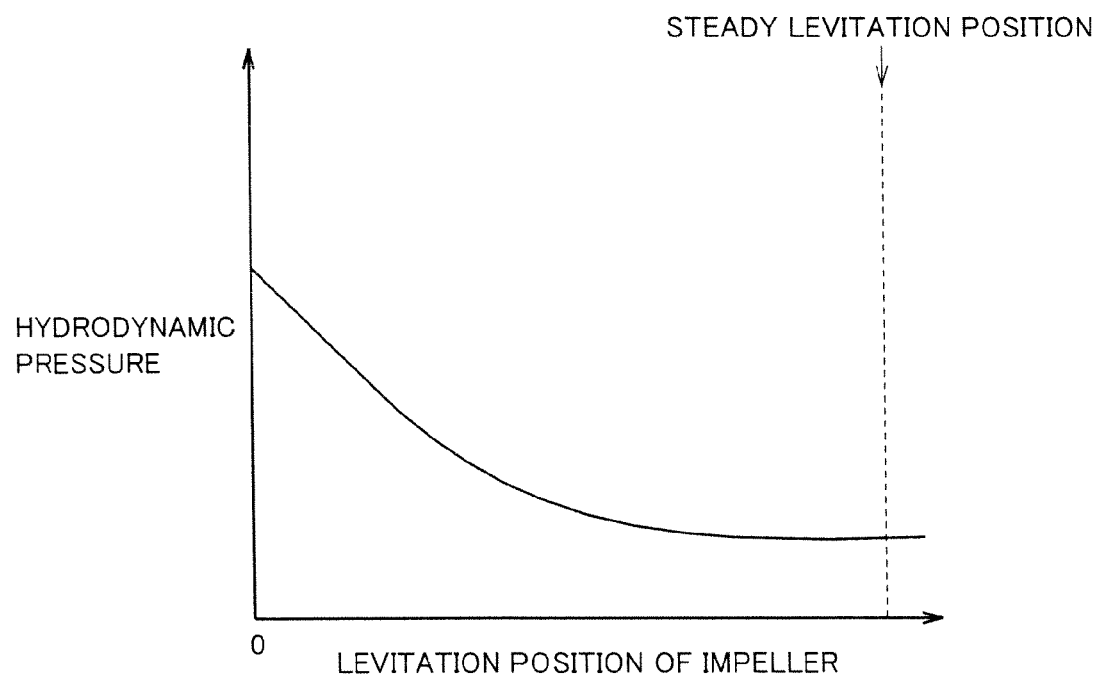
FIG. 10 is a diagram showing relation between a levitation position of the impeller and hydrodynamic pressure generated by groove for hydrodynamic bearing 21 shown in FIG. 9.
Figure 11:
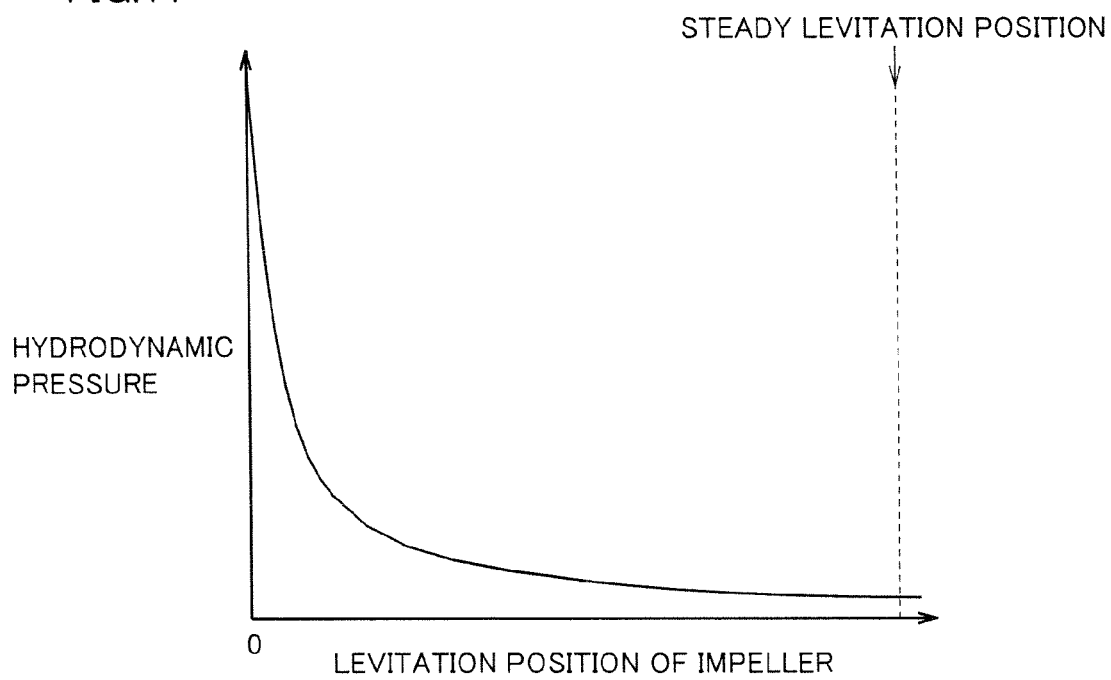
FIG. 11 is a diagram showing relation between a levitation position of the impeller and hydrodynamic pressure generated by groove for hydrodynamic bearing 22 shown in FIG. 9.
Figure 12:
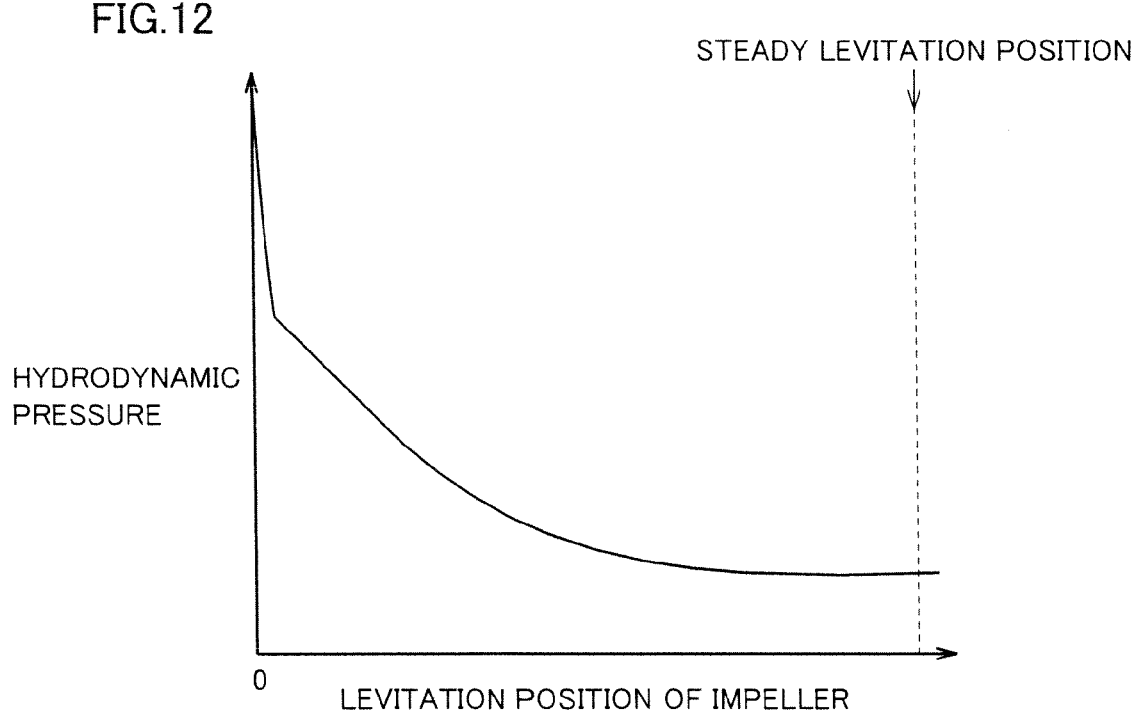
FIG. 12 is a diagram of FIGS. 10 and 11 as combined.

FIG. 10 is a diagram showing relation between a levitation position of impeller 10 when viewed from the surface of diaphragm 6 and hydrodynamic pressure received by impeller 10 from groove for hydrodynamic bearing 21 when impeller 10 is rotated at a prescribed rotation speed. FIG. 11 is a diagram showing relation between a distance between impeller 10 and diaphragm 6 and hydrodynamic pressure received by impeller 10 from groove for hydrodynamic bearing 22 when impeller 10 is rotated at a prescribed rotation speed. FIG. 12 is a diagram showing FIGS. 10 and 11 as combined.

As can be seen in FIGS. 10 to 12, groove for hydrodynamic bearing 21 generates hydrodynamic pressure higher than that generated by groove for hydrodynamic bearing 22 when a distance between impeller 10 and diaphragm 6 is long. Meanwhile, groove for hydrodynamic bearing 22 generates hydrodynamic pressure higher than that generated by groove for hydrodynamic bearing 21 when a distance between impeller 10 and diaphragm 6 is short. Therefore, in the invention of the subject application, since both of grooves for hydrodynamic bearing 21 and 22 are provided, high hydrodynamic pressure can be obtained in both cases of activation for rotation and steady rotation.

In this manner, owing to the hydrodynamic bearing effect produced between impeller 10 and grooves for hydrodynamic bearing 21, 22, impeller 10 moves away from diaphragm 6 and rotates without contacting. Accordingly, impeller 10 is smoothly activated to rotate and a blood flow path is secured between impeller 10 and diaphragm 6, thus preventing occurrence of blood accumulation therebetween and the resultant thrombus. Further, in a normal state, grooves for hydrodynamic bearing 21, 22 perform a stirring function between impeller 10 and diaphragm 6, thus preventing occurrence of partial blood accumulation therebetween.

Instead of providing grooves for hydrodynamic bearing 21, 22 in diaphragm 6, grooves for hydrodynamic bearing 21, 22 may be provided in a surface of shroud 12 of impeller 10.

It is preferable that a corner portion of each of grooves for hydrodynamic bearing 21, 22 be rounded to have R of at least 0.05 mm. As a result, occurrence of hemolysis can further be reduced.

Figure 13:
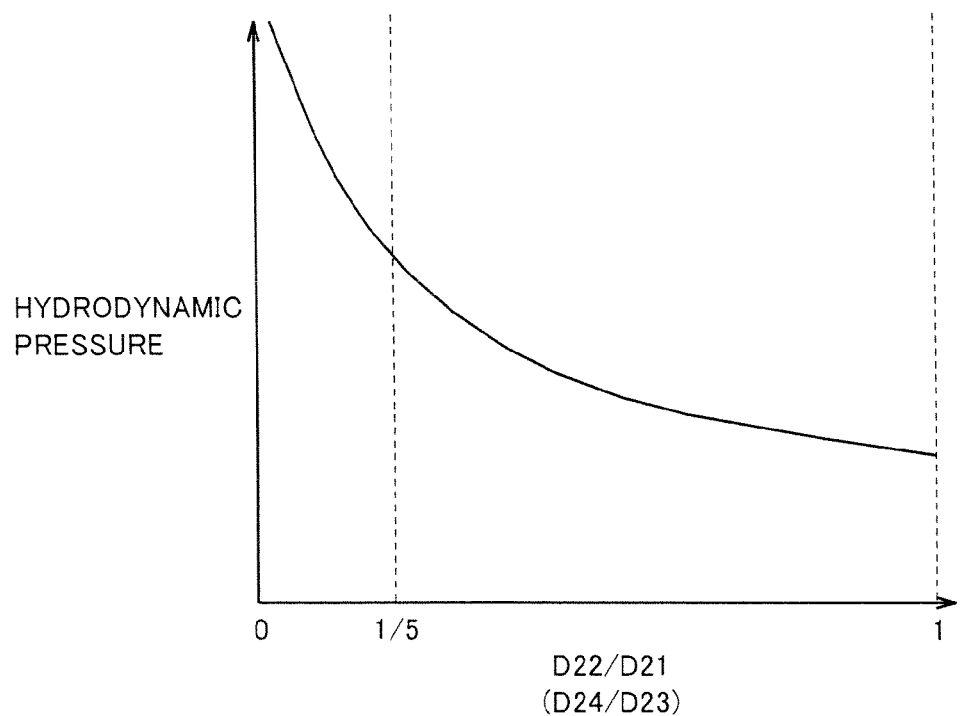
FIG. 13 is a diagram showing relation between a ratio between depths of grooves for hydrodynamic bearing 22, 21 (or grooves for hydrodynamic bearing 24, 23) and hydrodynamic pressure.

FIG. 13 is a diagram showing relation between a ratio D22/D21 between a depth D22 of groove for hydrodynamic bearing 22 and a depth D21 of groove for hydrodynamic bearing 21 and hydrodynamic pressure acting on impeller 21 while impeller 21 is located at a steady rotation levitation position. As shown in FIG. 12, in a case where impeller 21 is located at a position proximate to diaphragm 6, high hydrodynamic pressure is generated by adding groove for hydrodynamic bearing 22. As shown in FIG. 13, however, when impeller 21 is located at a steady rotation levitation position, hydrodynamic pressure lowers by adding groove for hydrodynamic bearing 22. Therefore, a depth and a width of groove for hydrodynamic bearing 22 should be determined such that lowering in hydrodynamic pressure or rigidity caused by addition of groove for hydrodynamic bearing 22 does not adversely affect pump performance. As shown in FIG. 13, as ratio D22/D21 is lower, lowering in hydrodynamic pressure at the steady rotation levitation position can be suppressed. Therefore, preferably, ratio D22/D21 is set to 1/5 or lower.

Figure 14:
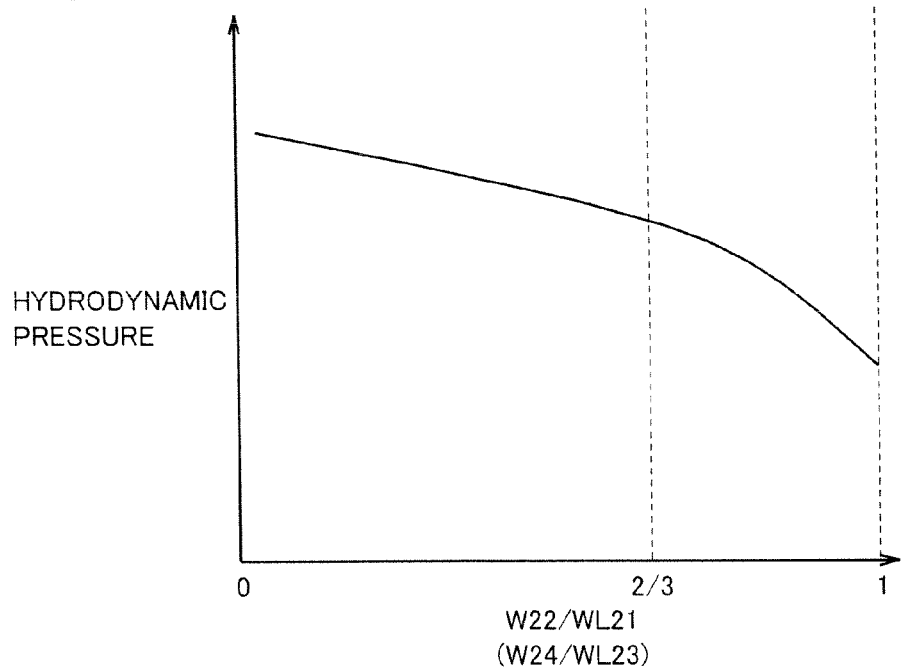
FIG. 14 is a diagram showing relation between a ratio between a width of groove for hydrodynamic bearing 22 and an interval between grooves for hydrodynamic bearing 21 (or a width of groove for hydrodynamic bearing 24 and an interval between grooves for hydrodynamic bearing 23) and hydrodynamic pressure.

FIG. 14 is a diagram showing relation between a ratio W22/WL21 between a width W22 of groove for hydrodynamic bearing 22 and an interval between grooves for hydrodynamic bearing 21 (a width of a land portion between grooves for hydrodynamic bearing 21) WL21 while impeller 21 is located at a steady levitation position and hydrodynamic pressure acting on impeller 21. As shown in FIG. 14, as ratio W22/WL21 is lower, lowering in hydrodynamic pressure at the steady rotation levitation position can be suppressed. Therefore, preferably, ratio W22/WL21 is set to 2/3 or lower.

Figure 6:
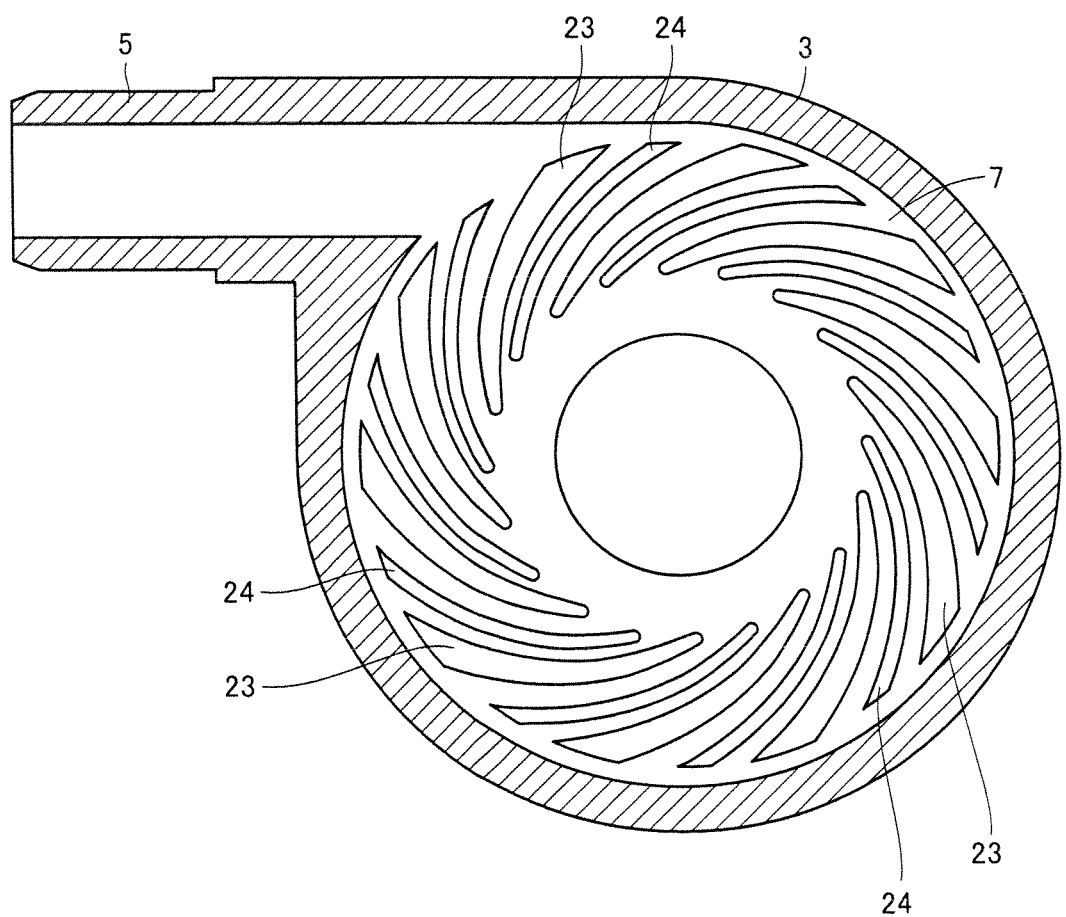
FIG. 6 is a cross-sectional view showing the state where the impeller has been removed from a cross-sectional view along the line VI-VI in FIG. 3.

As with the plurality of grooves for hydrodynamic bearing 21 and the plurality of grooves for hydrodynamic bearing 22, as shown in FIG. 6, the plurality of grooves for hydrodynamic bearing 23 and the plurality of grooves for hydrodynamic bearing 24 are formed with a size corresponding to shroud 11 of impeller 10. Each of grooves for hydrodynamic bearing 23, 24 has one end on the edge (circumference) of the circular portion slightly distant from the center of the inner wall of blood chamber 7, and extends spirally (in other words. in a curved manner) toward the portion near the outer edge of the inner wall of blood chamber 7 such that grooves for hydrodynamic bearing 23, 24 gradually increase in width. The plurality of grooves for hydrodynamic hearing 23 have substantially the same shape and they are arranged at substantially regular intervals. Groove for hydrodynamic hearing 23 is a concave portion and it preferably has a depth of about 0.005 to 0.4 mm. It is preferable that about 6 to 36 grooves for hydrodynamic bearing 23 be provided. In FIG. 6, ten grooves for hydrodynamic bearing 23 are equiangularly arranged with respect to the central axis of impeller 10.

The plurality of grooves for hydrodynamic bearing 24 have substantially the same shape and they are arranged at regular angular intervals in the direction of rotation of impeller 10. Groove for hydrodynamic bearing 24 is a concave portion and it preferably has a depth of about 0.005 to 0.3 mm. It is preferable that about 6 to 36 grooves for hydrodynamic bearing 24 be provided.

As description of grooves for hydrodynamic bearing 21, 22 has been given with reference to FIG. 9, groove for hydrodynamic bearing 24 is shallower than groove for hydrodynamic bearing 23. Groove for hydrodynamic bearing 24 has a depth preferably not greater than one fifth as great as a depth of groove for hydrodynamic bearing 23. In addition, groove for hydrodynamic bearing 24 has a width preferably not greater than two thirds as great as an interval between two grooves for hydrodynamic bearing 23. Further, the number of grooves for hydrodynamic bearing 24 is preferably equal to or smaller than the number of grooves for hydrodynamic bearing 23.

In FIG. 6, ten grooves for hydrodynamic bearing 23 and ten grooves for hydrodynamic bearing 24 are arranged at regular angular intervals with respect to the central axis of impeller 10. Since each of grooves for hydrodynamic bearing 23, 24 has a so-called inward spiral groove shape, clockwise rotation of impeller 10 causes increase in liquid pressure from an outer diameter portion toward an inner diameter portion of grooves for hydrodynamic bearing 23, 24. As a result, repulsion force is generated between impeller 10 and the inner wall of blood chamber 7 and it acts as hydrodynamic pressure.

As description of grooves for hydrodynamic bearing 21, 22 has been given with reference to FIGS. 10 to 12, groove for hydrodynamic bearing 23 generates hydrodynamic pressure higher than that generated by groove for hydrodynamic bearing 24 when a distance between impeller 10 and the inner wall of blood chamber 7 is long. Meanwhile, groove for hydrodynamic bearing 24 generates hydrodynamic pressure higher than that generated by groove for hydrodynamic bearing 23 when a distance between impeller 10 and the inner wall of blood chamber 7 is short. Therefore, in the invention of the subject application, since both of grooves for hydrodynamic bearing 23 and 24 are provided, high hydrodynamic pressure can be obtained in both cases of activation for rotation and steady rotation.

In this manner, owing to the hydrodynamic bearing effect produced between impeller 10 and grooves for hydrodynamic bearing 23, 24, impeller 10 moves away from the inner wall of blood chamber 7 and rotates without contacting. Accordingly, impeller 10 is smoothly activated to rotate and a blood flow path is secured between impeller 10 and the inner wall of blood chamber 7, thus preventing occurrence of blood accumulation therebetween and the resultant thrombus. Further, in a normal state, grooves for hydrodynamic bearing 23, 24 perform a stirring function between impeller 10 and the inner wall of blood chamber 7, thus preventing occurrence of partial blood accumulation therebetween. In addition, when pump unit 1 is subjected to external impact or when the hydrodynamic pressure by grooves for hydrodynamic bearing 21, 22 becomes excessive, impeller 10 can be prevented from being in close contact with the inner wall of blood chamber 7. The hydrodynamic pressure generated by grooves for hydrodynamic bearing 21, 22 may be different from the hydrodynamic pressure generated by grooves for hydrodynamic bearing 23, 24.

Instead of providing grooves for hydrodynamic bearing 23, 24 in the inner wall of blood chamber 7, grooves for hydrodynamic bearing 23, 24 may be provided in a surface of shroud 11 of impeller 10.

It is preferable that a corner portion of each of grooves for hydrodynamic bearing 23, 24 be rounded to have R of at least 0.05 mm. As a result, occurrence of hemolysis can further be reduced.

In addition, as description of grooves for hydrodynamic bearing 21, 22 has been given with reference to FIGS. 13 and 14, a ratio D24/D23 between a depth D24 of groove for hydrodynamic bearing 24 and a depth D23 of groove for hydrodynamic bearing 23 is set to 1/5 or lower. Moreover, a ratio W24/WL23 between a width W24 of groove for hydrodynamic bearing 24 and an interval between grooves for hydrodynamic bearing 23 (a width of a land portion between grooves for hydrodynamic bearing 23) WL23 is set to 2/3 or lower.

Further, it is preferable that impeller 10 rotate in a state where a gap between shroud 12 of impeller 10 and diaphragm 6 is substantially equal to a gap between shroud 11 of impeller 10 and the inner wall of blood chamber 7. If one of the gaps becomes narrower due to serious disturbance such as hydrodynamic force acting on impeller 10, it is preferable that grooves for hydrodynamic bearing 21, 22 and 23, 24 have different shapes so that hydrodynamic pressure generated by the grooves for hydrodynamic bearing on the narrower side becomes higher than the hydrodynamic pressure generated by the other grooves for hydrodynamic bearing to make the gaps substantially equal to each other.

While each of grooves for hydrodynamic bearing 21 to 24 has the inward spiral groove shape in FIGS. 5 and 6, grooves for hydrodynamic bearing 21 to 24 having another shape may be used. Nevertheless, for blood circulation, it is preferable to employ grooves for hydrodynamic bearing 21 to 24 having the inward spiral groove shape that allows a smooth flow of blood.

Figure 15:
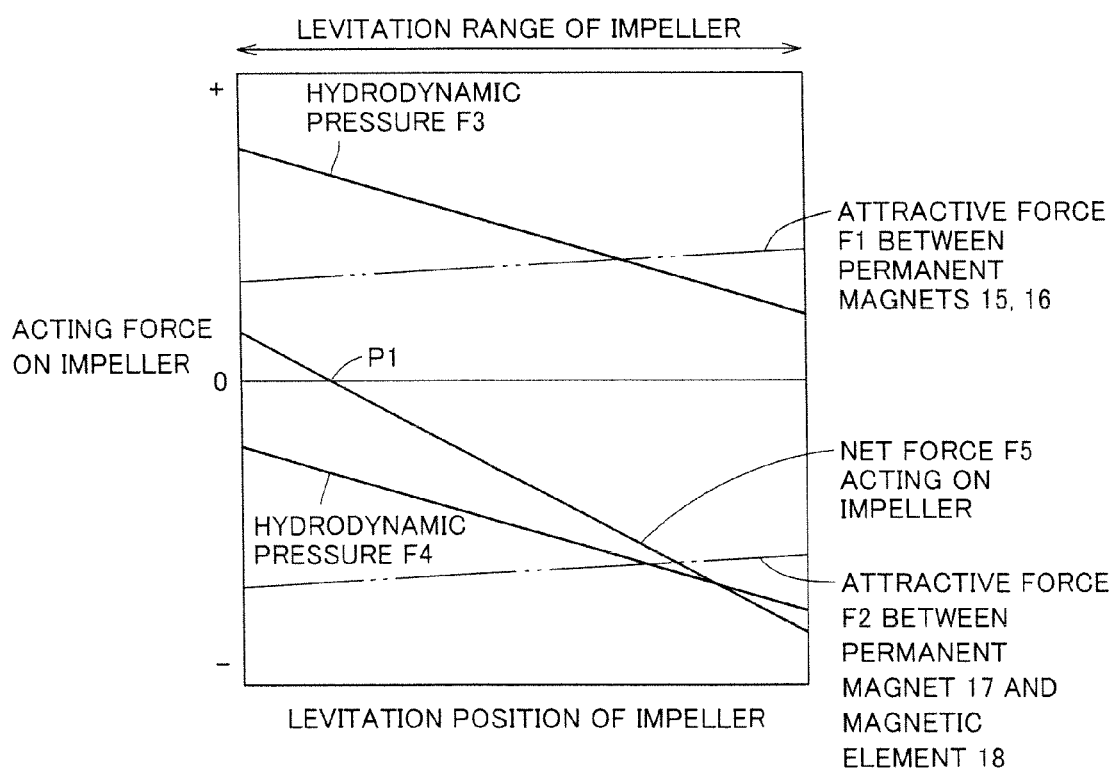
FIG. 15 is a diagram showing relation between a levitation position of the impeller and force acting on the impeller.

FIG. 15 is a diagram showing forces acting on impeller 10 when magnitude of a resultant force of an attractive force F1 between permanent magnets 15 and 16 and an attractive force F2 between permanent magnet 17 and magnetic element 18 is adjusted to zero at a position P1 other than a central position of the movable range of impeller 10 in blood chamber 7. The rotation speed of impeller 10 is kept at a rated value.

That is, it is assumed that attractive force F1 between permanent magnets 15 and 16 is set to be smaller than attractive force F2 between permanent magnet 17 and magnetic element 18 and a levitation position of impeller 10 where their resultant force becomes zero is on the diaphragm 6 side relative to the center of the movable range of the impeller. Grooves for hydrodynamic bearing 21, 22 and grooves for hydrodynamic bearing 23, 24 have the same shape.

A horizontal axis of FIG. 15 represents a position of impeller 10 (the left side in the figure being the diaphragm 6 side) and a vertical axis represents forces acting on impeller 10. Force acting on impeller 10 toward the diaphragm 6 side is expressed as a negative acting force. As the forces acting on impeller 10, attractive force F1 between permanent magnets 15 and 16, attractive force F2 between permanent magnet 17 and magnetic element 18, a hydrodynamic pressure F3 generated by grooves for hydrodynamic bearing 21, 22, a hydrodynamic pressure F4 generated by grooves for hydrodynamic hearing 23, 24, and a "net force F5 acting on impeller" which is their resultant force are illustrated.

As can be seen in FIG. 15, at a position where net force F5 acting on impeller 10 becomes zero, the levitation position of impeller 10 is significantly deviated from the central position of the movable range of impeller 10. As a result, a distance between rotating impeller 10 and diaphragm 6 becomes narrower, and impeller 10 is brought into contact with diaphragm 6 even by the action of a small disturbance force on impeller 10.

Figure 16:
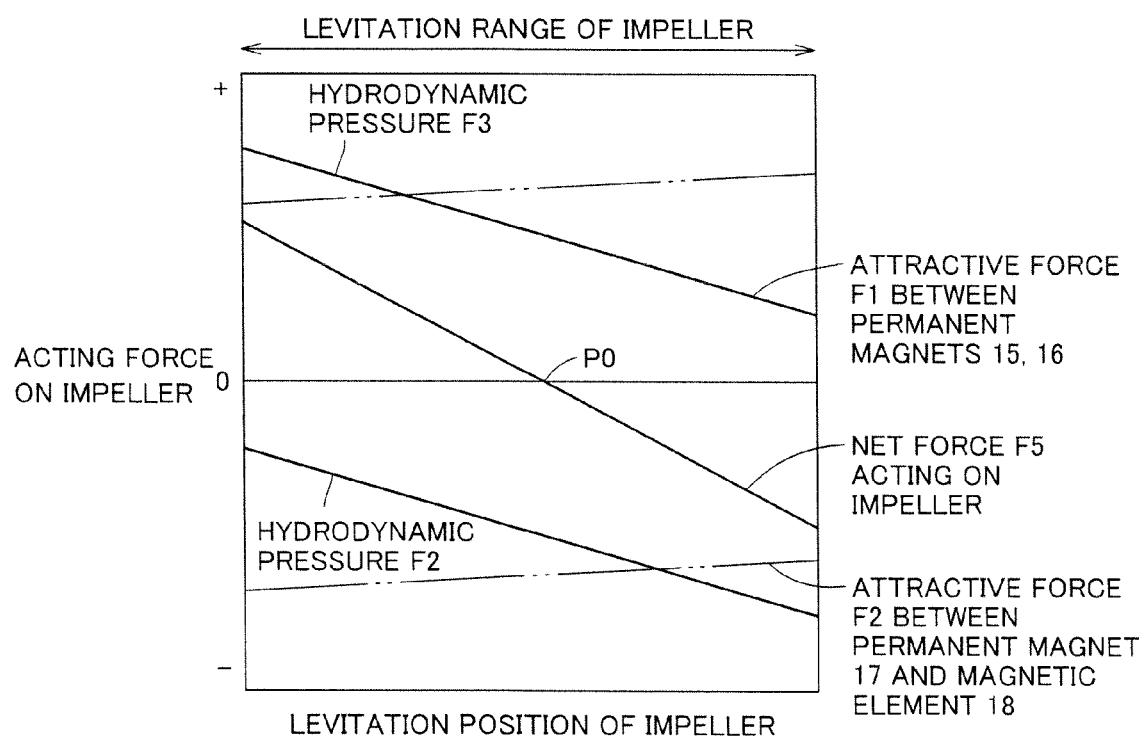
FIG. 16 is another diagram showing relation between a levitation position of the impeller and force acting on the impeller.

In contrast, FIG. 16 illustrates forces acting on impeller 10 when a magnitude of the resultant force of attractive force F1 between permanent magnets 15 and 16 and attractive force F2 between permanent magnet 17 and magnetic element 18 is adjusted to zero at a central position P0 of the movable range of impeller 10 in blood chamber 7. The rotation speed of impeller 10 is kept at the rated value in this case as well.

Namely, attractive force F1 between permanent magnets 15 and 16 and attractive force F2 between permanent magnet 17 and magnetic element 18 are set to be substantially equal to each other. In addition, grooves for hydrodynamic bearing 21, 22 and grooves for hydrodynamic bearing 23, 24 have the same shape. In this case, supporting rigidity for the levitation position of impeller 10 is higher than in the example shown in FIG. 15. Further, since net force F5 acting on impeller 10 is zero at the center of the movable range, impeller 10 is levitated at the central position when a disturbance force is not acting on impeller 10.

As such, a levitation position of impeller 10 is determined by balance among attractive force F1 between permanent magnets 15 and 16, attractive force F2 between permanent magnet 17 and magnetic element 18, hydrodynamic pressure F3 generated by grooves for hydrodynamic bearing 21, 22 during rotation of impeller 10, and hydrodynamic pressure F4 generated by grooves for hydrodynamic bearing 23, 24 during rotation of impeller 10. By making F1 and F2 substantially equal to each other and by forming grooves for hydrodynamic hearing 21, 22 and grooves for hydrodynamic bearing 23, 24 in the same shape, impeller 10 can be levitated substantially in a central portion of blood chamber 7 during rotation of impeller 10. Since impeller 10 has such a shape that vanes are formed between two discs as shown in FIGS. 3 and 4, two surfaces facing the inner wall of housing 2 can be formed to have the same shape and the same dimensions. Therefore, it is possible to provide grooves for hydrodynamic bearing 21, 22 and grooves for hydrodynamic bearing 23, 24 having a function to generate substantially the same hydrodynamic pressure on both sides of impeller 10.

In this case, impeller 10 is levitated at the central position of blood chamber 7 and thus held at a position farthest from the inner wall of housing 2. As a result, even if the levitation position of impeller 10 is changed due to application of a disturbance force to levitated impeller 10, the possibility that impeller 10 is brought into contact with the inner wall of housing 2 is lowered, thus also lowering the possibility of occurrence of thrombus and hemolysis resulting from such contact.

While grooves for hydrodynamic bearing 21, 22 and grooves for hydrodynamic bearing 23, 24 have the same shape in the examples shown in FIGS. 15 and 16, grooves for hydrodynamic bearing 21, 22 may be different in shape and hydrodynamic pressure generating function from grooves for hydrodynamic hearing 23, 24. For example, when disturbance acts on impeller 10 always in one direction due to hydrodynamic force or the like during pumping, performance of a groove for hydrodynamic bearing in the disturbance direction may be made higher than performance of the other groove for hydrodynamic bearing, thereby levitating and rotating impeller 10 at the central position of housing 2. As a result, the probability of contact between impeller 10 and housing 2 can be lowered, thereby attaining stable levitation performance of impeller 10.

Furthermore, when an absolute value of a negative axial supporting rigidity value of impeller 10 which is constituted of attractive force F1 between permanent magnets 15 and 16 and attractive force F2 between permanent magnet 17 and magnetic element 18 is expressed as Ka, an absolute value of a positive radial rigidity value is expressed as Kr, and an absolute value of a positive rigidity value obtained by grooves for hydrodynamic bearing 21 to 24 in a normal rotation speed range where impeller 10 rotates is expressed as Kg, it is preferable that relation of Kg>Ka+Kr be satisfied.

Specifically, when absolute value Ka of the negative axial rigidity value is 20000 N/m and absolute value Kr of the positive radial rigidity value is 10000 N/m, absolute value Kg of the positive rigidity value obtained by grooves for hydrodynamic bearing 21 to 24 in the rotation speed range where impeller 10 normally rotates is set to a value higher than 30000 N/m.

The axial supporting rigidity for impeller 10 is a value obtained by subtracting negative rigidity due to the attractive force between the magnetic elements and the like from rigidity resulting from the hydrodynamic pressure generated by grooves for hydrodynamic bearing 21 to 24. Thus, by satisfying relation of Kg>Ka+Kr, the axial supporting rigidity for impeller 10 can be made higher than the radial supporting rigidity. With such setting, movement of impeller 10 can be suppressed more in the axial direction than in the radial direction when a disturbance force acts on impeller 10, thereby avoiding mechanical contact between impeller 10 and housing 2 in a portion where grooves for hydrodynamic bearing 21 to 24 are formed.

In particular, since grooves for hydrodynamic bearing 21 to 24 are provided as concave portions in planar surfaces as shown in FIGS. 3, 5 and 6, mechanical contact between housing 2 and impeller 10 in these portions during rotation of impeller 10 may result in damage to one or both of a surface of impeller 10 and a surface of the inner wall of housing 2 (projections and recesses in the surfaces), and blood passage through this portion may cause occurrence of thrombus and hemolysis. In order to prevent mechanical contact at grooves for hydrodynamic bearing 21 to 24 to suppress thrombus and hemolysis, it is effective to make the axial rigidity higher than the radial rigidity.

Whirl occurs in unbalanced impeller 10 during rotation, and this whirl is greatest when a natural frequency determined by the mass of impeller 10 and the supporting rigidity value of impeller 10 matches the rotation speed of impeller 10.

Since the radial supporting rigidity for impeller 10 is smaller than the axial supporting rigidity in pump unit 1, it is preferable to set a maximum rotation speed of impeller 10 to be equal to or lower than the radial natural frequency. Accordingly, in order to prevent mechanical contact between impeller 10 and housing 2, when a radial rigidity value of impeller 10 which is constituted of attractive force F1 between permanent magnets 15 and 16 and attractive force F2 between permanent magnet 17 and magnetic element 18 is expressed as Kr (N/m), the mass of impeller 10 is expressed as m (kg), and the rotation speed of the impeller is expressed as ω (rad/s), it is preferable that relation of $\omega < (Kr/m)^{0.5}$ be satisfied.

Specifically, when the mass of impeller 10 is 0.03 kg and the radial rigidity value is 2000 N/m, the maximum rotation speed of impeller 10 is set to 258 rad/s (2465 rpm) or lower. Conversely, when the maximum rotation speed of impeller 10 is set to 366 rad/s (3500 rpm), the radial rigidity is set to 4018 N/m or higher.

It is further preferable to set the maximum rotation speed of impeller 10 to 80% or lower of this ω. Specifically, when the mass of impeller 10 is 0.03 kg and the radial rigidity value is 2000 N/m, the maximum rotation speed is set to 206.4 rad/s (1971 rpm) or lower. Conversely, when it is desired to set the maximum rotation speed of impeller 10 to 366 rad/s (3500 rpm), the radial rigidity value is set to 6279 N/m or higher. By thus setting the maximum rotation speed of impeller 10, contact between rotating impeller 10 and housing 2 can be suppressed.

When the rigidity due to the hydrodynamic pressure generated by grooves for hydrodynamic bearing 21 to 24 becomes higher than the negative axial rigidity value of impeller 10 which is constituted of attractive force F1 between permanent magnets 15 and 16 and attractive force F2 between permanent magnet 17 and magnetic element 18, impeller 10 and housing 2 are not in contact with each other. It is thus preferable to minimize this negative rigidity value. In order to keep the negative rigidity value low, it is preferable that the surfaces facing each other of permanent magnets 15 and 16 have different sizes. For example, by making the size of permanent magnet 16 smaller than that of permanent magnet 15, a rate of change in attractive force that varies with a distance between the magnets, that is, the negative rigidity, can be minimized, thereby preventing lowering in supporting rigidity for the impeller.

It is also preferable to check to see that impeller 10 is in contact with diaphragm 6 before activating impeller 10 to rotate.

Namely, when impeller 10 is not rotating, impeller 10 is not supported without contacting by grooves for hydrodynamic bearing 21 to 24, but is in contact with housing 2 with high surface pressure due to attractive force F1 between permanent magnets 15 and 16 and attractive force F2 between permanent magnet 17 and magnetic element 18. Further, when impeller 10 is rotated by magnetic interaction between coil 20 and magnetic element 18 in motor chamber 8 and permanent magnet 17 in impeller 10 as in pump unit 1, starting torque is smaller than in an example where an impeller is driven to rotate through magnetic coupling between permanent magnets as shown in FIG. 3 of PTL 2. It is thus difficult to smoothly activate impeller 10 to rotate.

When shroud 12 of impeller 10 is in contact with diaphragm 6, however. permanent magnet 17 in impeller 10 and magnetic element 18 in motor chamber 8 are closer to each other than when shroud 11 of impeller 10 is in contact with the inner wall of blood chamber 7, which allows increase in rotational torque during activation of impeller 10, thereby smoothly activating impeller 10 to rotate.

As described above, however, when impeller 10 is rotating, attractive force F1 between permanent magnets 15 and 16 and attractive force F2 between permanent magnet 17 and magnetic element 18 are set to be balanced with each other around the center of the movable range of impeller 10. Thus, impeller 10 is not necessarily in contact with diaphragm 6 when impeller 10 is not rotating.

For this reason, this centrifugal blood pump apparatus is provided with means for moving impeller 10 toward diaphragm 6 before activating impeller 10 to rotate. Specifically, a current is fed through the plurality of coils 20 such that attractive force F2 between permanent magnet 17 and magnetic element 18 becomes higher, to move impeller 10 toward diaphragm 6.

Figure 17:
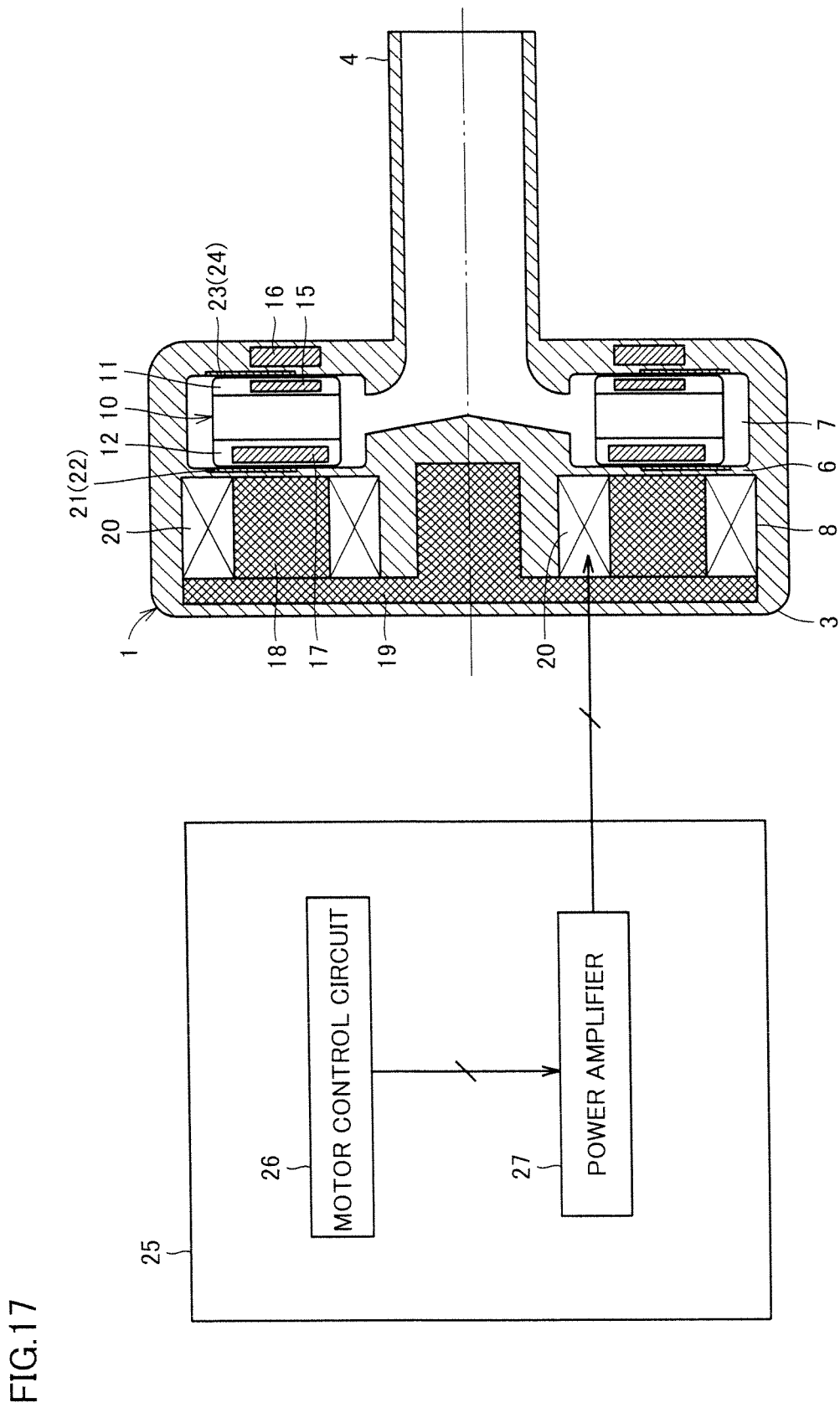
FIG. 17 is a block diagram showing a configuration of a controller for controlling the pump unit shown in FIGS. 1 to 7.

FIG. 17 is a block diagram showing a configuration of a controller 25 for controlling pump unit 1. In FIG. 17, controller 25 includes a motor control circuit 26 and a power amplifier 27. Motor control circuit 26 outputs three-phase control signals in the power distribution system shifted by 120 degrees, for example. Power amplifier 27 amplifies the three-phase control signals from motor control circuit 26, and generates three-phase voltages VU, VV and VW shown in FIG. 8. Three-phase voltages VU, VV and VW are applied to first to third coils 20 described with reference to FIGS. 7 and 8, respectively. As a result, during normal operation, impeller 10 rotates at a prescribed rotation speed at the central position of the movable range.

Figure 18:
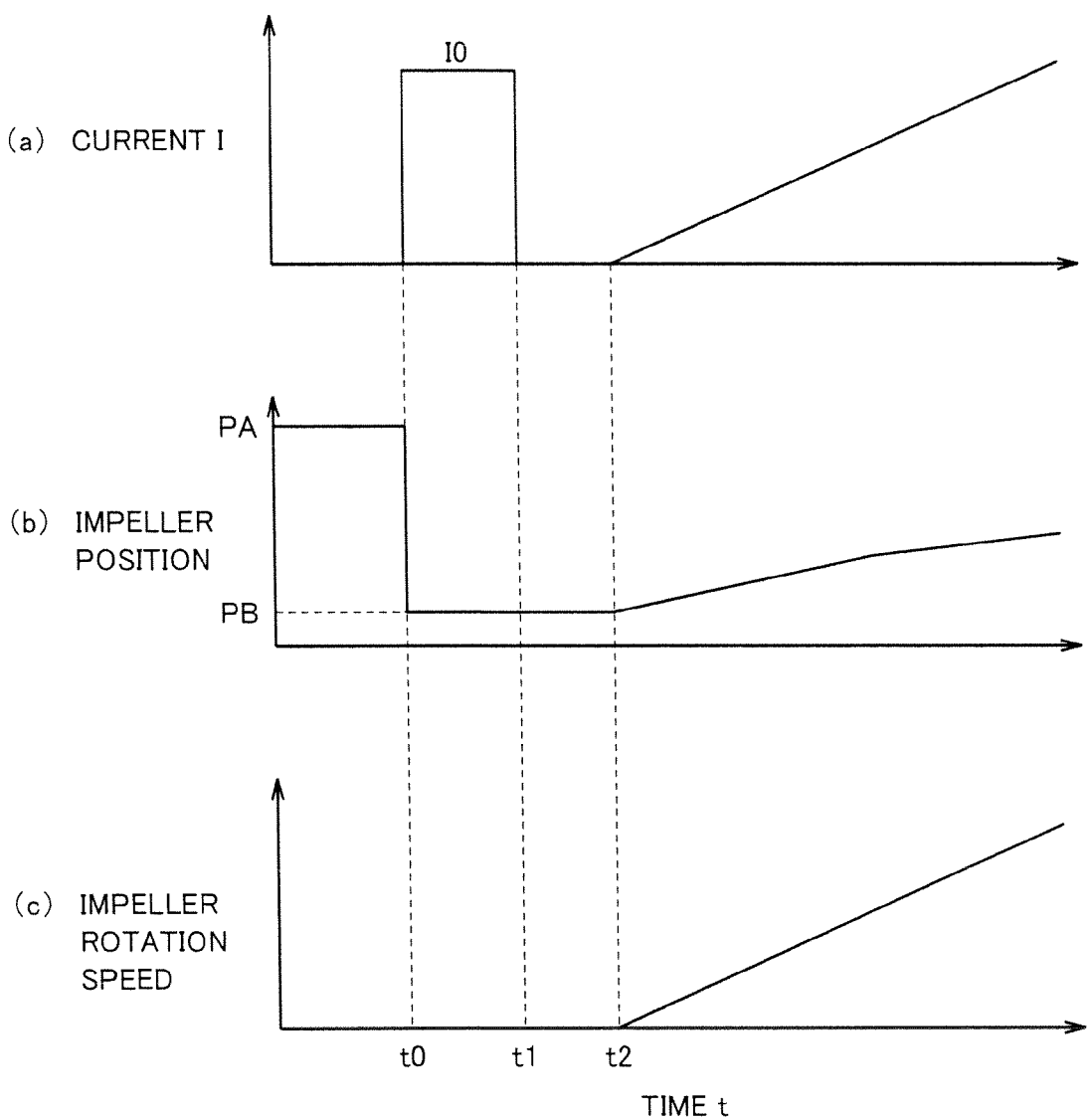
FIG. 18 is a time chart illustrating an operation of the controller shown in FIG. 17.

FIGS. 18 (a) to (c) are time charts illustrating temporal variations of a coil current I when impeller 10 is activated to rotate, a position of impeller 10, and a rotation speed of impeller 10. Referring to FIGS. 18 (a) to (c), it is assumed that, in an initial state, shroud 11 of impeller 10 is in contact with the inner wall of blood chamber 7 due to the attractive force between permanent magnets 15 and 16 and impeller 10 is at a position PA. Since it is difficult to rotate impeller 10 in this state, impeller 10 is moved to a position PB where shroud 12 of impeller 10 is in contact with diaphragm 6.

At time t0, voltages VU, VV and VW of any one of the six patterns (0 to 60 degrees, 60 to 120 degrees, . . . , 300 to 360 degrees) shown in FIG. 8 are applied to first to third coils 20, respectively, and a predetermined current I0 is fed through coils 20. When current I0 is fed through coils 20, attractive force F2 between permanent magnet 17 and magnetic element 18 becomes higher than attractive force F1 between permanent magnets 15 and 16, so that impeller 10 moves to position PB on the diaphragm 6 side with little rotation, causing shroud 12 of impeller 10 to be in contact with diaphragm 6. When impeller 10 moved to position PB, current I0 is cut off (time t1).

The reason for moving impeller 10 without rotating impeller 10 is that movement of rotating impeller 10 to position PB on the diaphragm 6 side is blocked by the hydrodynamic bearing effect of grooves for hydrodynamic bearing 21, 22. In addition, it is preferable to provide a sensor for detecting a position of impeller 10 in blood chamber 7 and check to see that impeller 10 is in contact with diaphragm 6 before cutting off current I0.

Then, three-phase voltages VU, VV and VW are applied to first to third coils 20 described with reference to FIG. 8, respectively, and coil current I is gradually increased to a predetermined rated value. Here, impeller 10 is in contact with diaphragm 6 and thus it smoothly rotates. With the increase in coil current I, impeller 10 moves from position PB on the diaphragm 6 side to the central position of the movable range.

When voltages VU, VV and VW of the six patterns (0 to 60 degrees, 60 to 120 degrees, . . . , 300 to 360 degrees) are applied to first to third coils 20 during activation, respectively, a pattern where the attractive force between permanent magnet 17 and magnetic element 18 becomes maximum varies with positional relation between permanent magnet 17 and magnetic element 18. Thus, instead of applying only voltages VU, VV and VW of a constant pattern to first to third coils 20 during activation, respectively, voltages VU, VV and VW of the six patterns may successively be applied to first to third coils 20 for a prescribed time period. In this case, impeller 10 slightly rotates (strictly speaking, quarter turn or less, i.e., rotation by 360 degrees or less in electrical angle) and moves to position PB on the diaphragm 6 side.

When voltages VU, VV and VW of the six patterns are applied, a current does not flow through any of first to third coils 20, six of nine magnetic elements 18 become the N-pole or the S-pole, and three remaining magnetic elements 18 do not generate a magnetic polarity. Thus, voltages that cause a current to flow through all of first to third coils 20 and each of nine magnetic elements 18 to become the N-pole or the S-pole may be applied to first to third coils 20, to increase attractive force between permanent magnet 17 and magnetic element 18.

Figure 19:
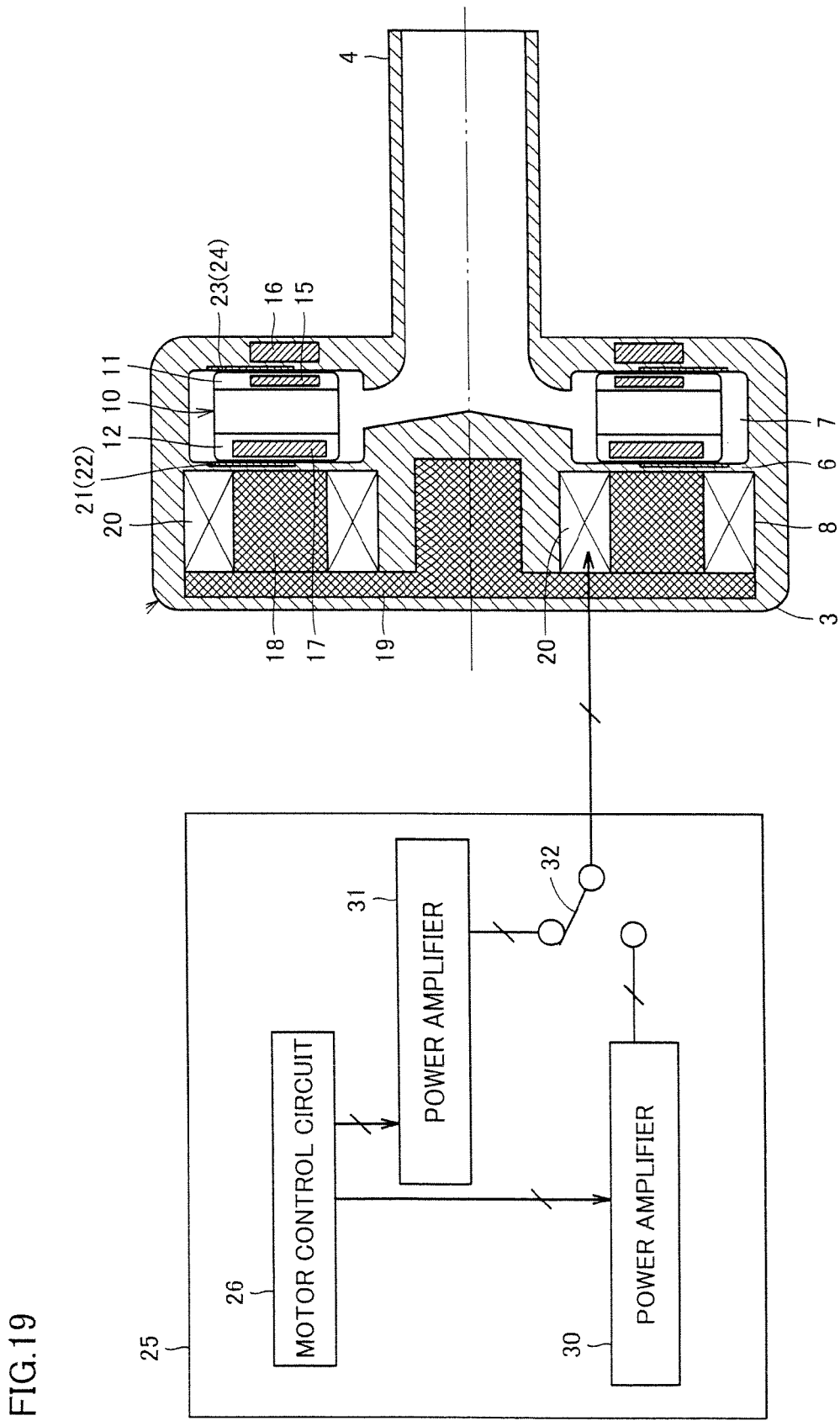
FIG. 19 is a block diagram showing a modification of the embodiment.

FIG. 19 is a block diagram showing a modification of the first embodiment. In this modification, a power source is switched between during activation of impeller 10 for rotation and a subsequent time period. Namely, referring to FIG. 19, in this modification, power amplifier 27 in FIG. 17 is replaced with power amplifiers 30, 31 and a switch 32. Between time t0 and t1 in FIG. 18, an output signal from motor control circuit 26 is provided to power amplifier 30 and an output voltage from power amplifier 30 is applied to coils 20 via switch 32, causing current I0 to flow through coils 20. After time t2, an output signal from motor control circuit 26 is provided to power amplifier 31 and an output voltage from power amplifier 31 is applied to coils 20 via switch 32, causing a current to flow through coils 20.

Figure 20:
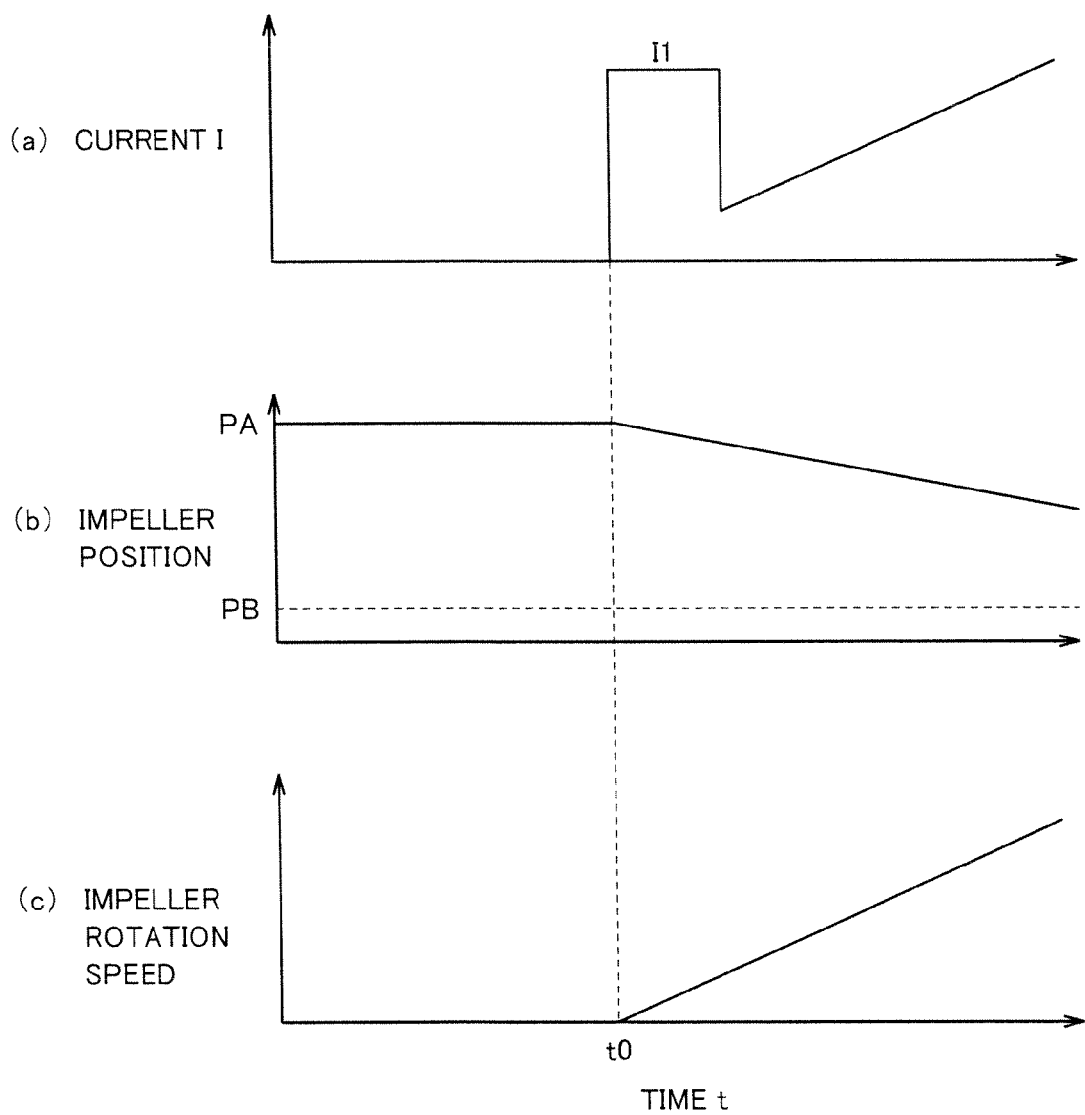
FIG. 20 is a time chart illustrating another modification of the embodiment.

FIGS. 20 (a) to (c) are time charts illustrating another modification of the first embodiment. Referring to FIGS. 20 (a) to (c), it is assumed that, in an initial state, shroud 11 of impeller 10 is in contact with the inner wall of blood chamber 7, and impeller 10 is at position PA. At time t0, a predetermined current I1 is fed through coils 20. That is, motor control circuit 26 outputs three-phase control signals in the power distribution system shifted by 120 degrees, for example. Power amplifier 27 amplifies the three-phase control signals from motor control circuit 26 and generates three-phase voltages VU, VV and VW shown in FIG. 8. Three-phase voltages VU, VV and VW are applied to first to third coils 20 described with reference to FIGS. 7 and 8, respectively.

Accordingly, a rotating magnetic field is applied to impeller 10 by current I1. Current I1 is larger than current I0 in FIG. 18 and it can activate impeller 10 to rotate even when shroud 11 of impeller 10 is in contact with the inner wall of blood chamber 7. After activation for rotation is confirmed, coil current I is reduced and gradually increased to the predetermined rated value. In this manner, even when impeller 10 is on the position PA side, an overcurrent may be fed through coils 20 only when impeller 10 is activated to rotate.

In addition, a diamond-like carbon (DLC) coating may be formed on at least one of the surface of the inner wall of blood chamber 7 and the surface of diaphragm 6, and the surface of impeller 10. As a result, frictional force between impeller 10, and the inner wall of blood chamber 7 and diaphragm 6 can be reduced to smoothly activate the impeller to rotate. A fluorine-based resin coating, a paraxylylene-based resin coating or the like may be formed instead of the diamond-like carbon coating.

Figure 21:
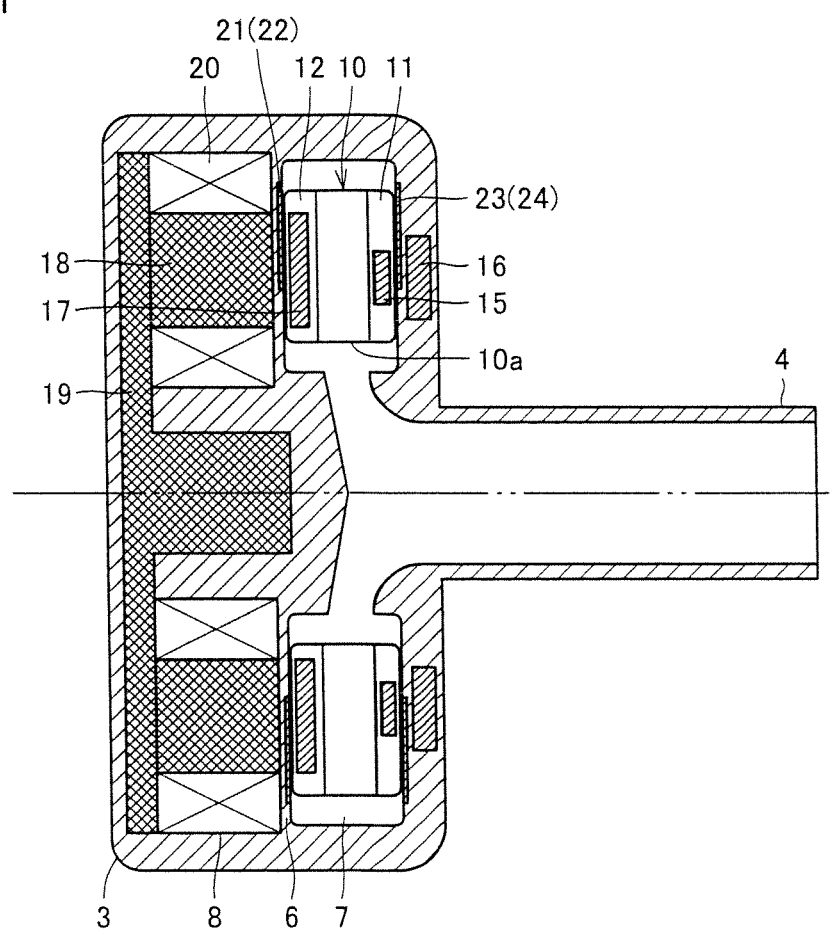
FIG. 21 is a cross-sectional view showing yet another modification of the embodiment.

FIG. 21 is a cross-sectional view showing yet another modification of the first embodiment, which is compared to FIG. 3. Referring to FIG. 21, in this modification, the surfaces facing each other of permanent magnets 15 and 16 have different sizes. While the surfaces facing each other of permanent magnets 15 and 16 have the same size in FIG. 3, by making the surfaces facing each other of permanent magnets 15 and 16 have different sizes, the amount of change in attractive force which varies with a distance between the magnets, that is, the negative rigidity, can be minimized, thereby preventing lowering in supporting rigidity for impeller 10.

Figure 22:
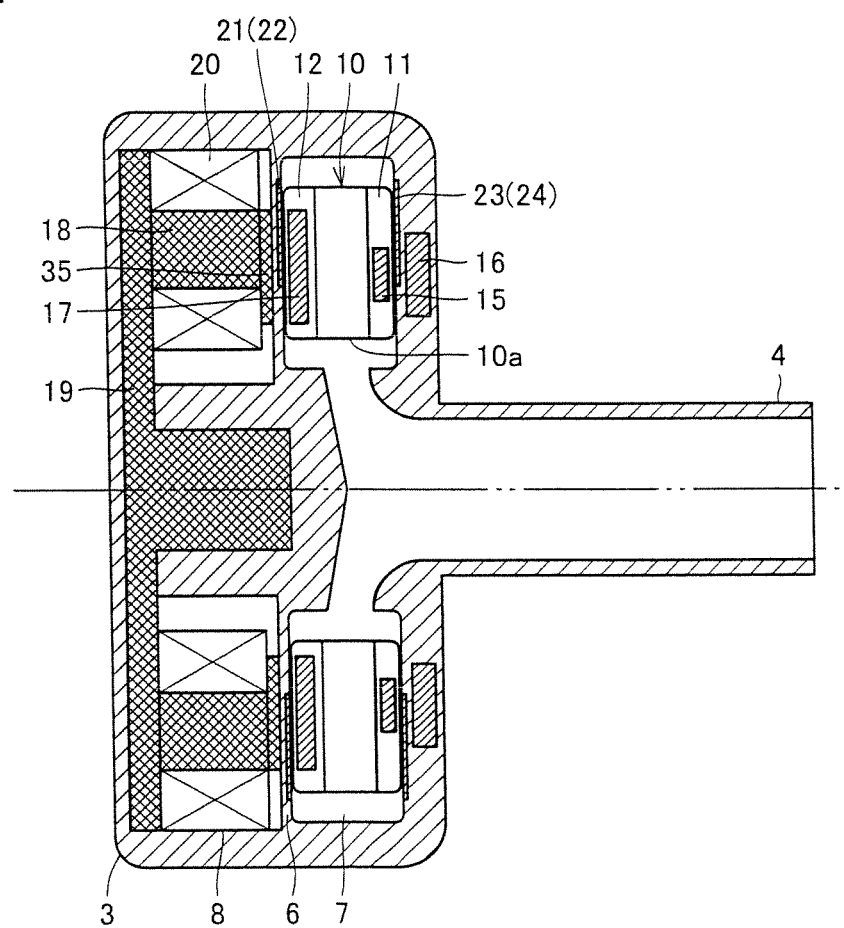
FIG. 22 is a cross-sectional view showing yet another modification of the embodiment.

FIG. 22 is a cross-sectional view showing yet another modification of the first embodiment, which is compared to FIG. 21. Referring to FIG. 22, in this modification, a magnetic element 35 is provided on a tip surface of each magnetic element 18 facing permanent magnet 17. A surface of magnetic element 35 facing permanent magnet 17 has an area larger than an area of the tip surface of magnetic element 18. In this modification, force of magnetic elements 18 and 35 attracting permanent magnet 17 can be increased, thus increasing energy efficiency when impeller 10 is driven to rotate.

Figure 23:
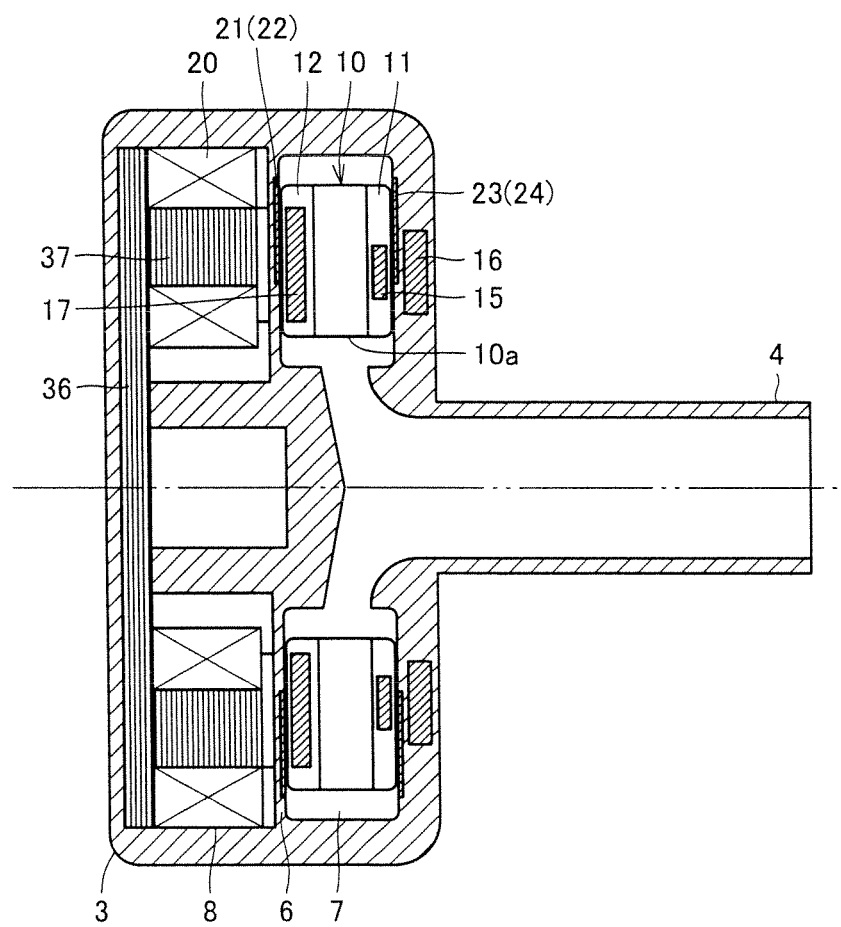
FIG. 23 is a cross-sectional view showing yet another modification of the embodiment.

FIG. 23 is a cross-sectional view showing yet another modification of the first embodiment, which is compared to FIG. 21. Referring to FIG. 23, in this modification, yoke 19 is replaced with a yoke 36 and magnetic element 18 is replaced with a magnetic element 37. Yoke 36 and magnetic element 37 each include a plurality of steel plates stacked in a length direction of a rotation axis of impeller 10. In this modification, eddy current loss that occurs in yoke 36 and magnetic element 37 can be reduced, thus increasing energy efficiency when impeller 10 is driven to rotate.

Figure 24:
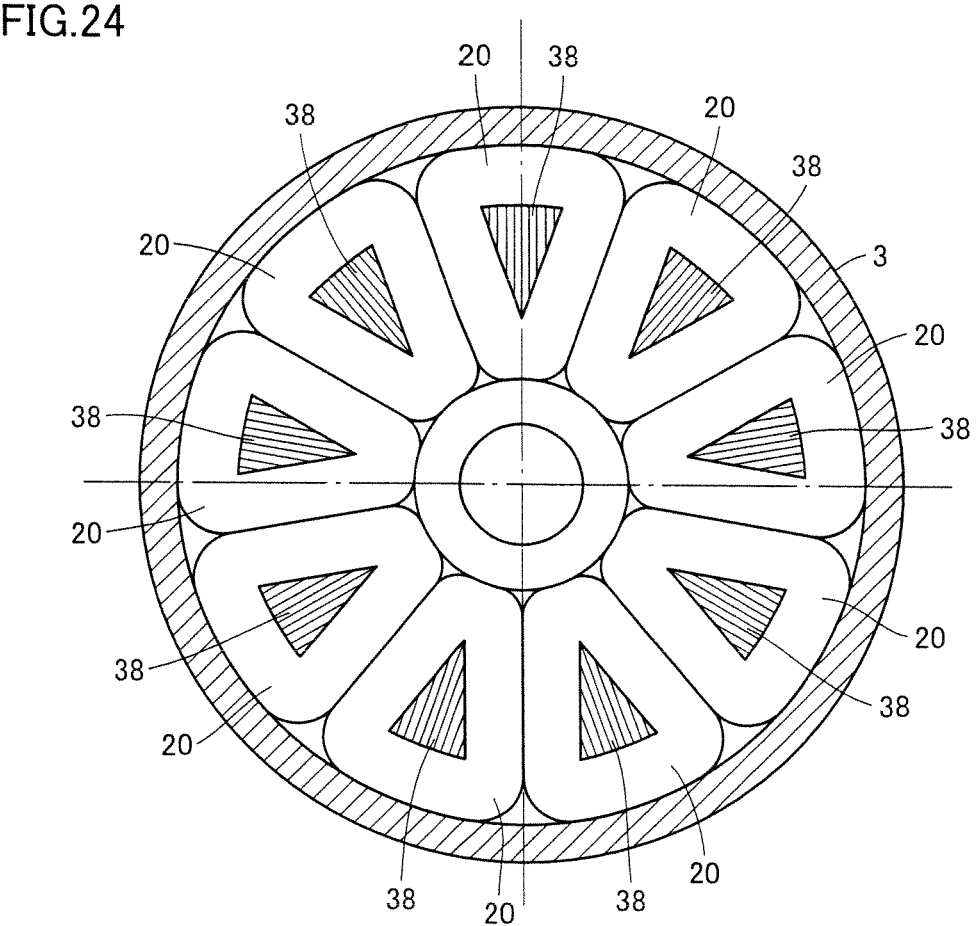
FIG. 24 is a cross-sectional view showing yet another modification of the embodiment.
Figure 25:
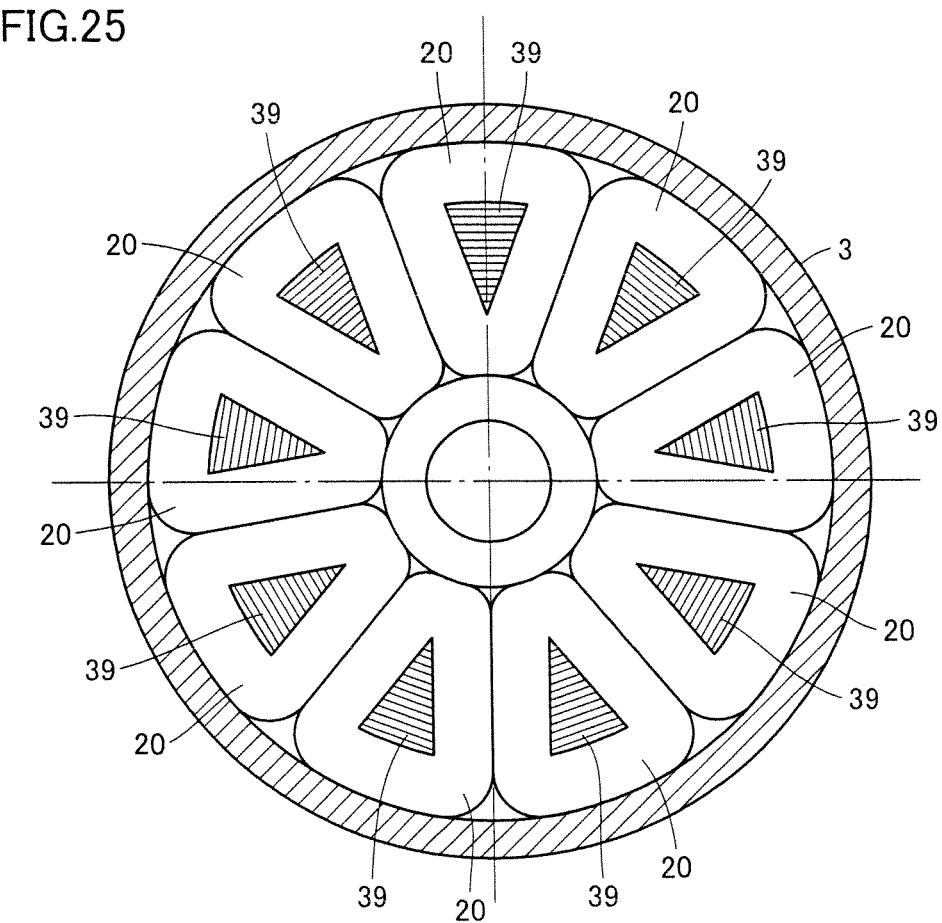
FIG. 25 is a cross-sectional view showing yet another modification of the embodiment.

Alternatively, as shown in FIG. 24, magnetic element 37 may be replaced with a magnetic element 38 including a plurality of steel plates stacked in a rotation direction of impeller 10. Alternatively, as shown in FIG. 25, magnetic element 37 may be replaced with a magnetic element 39 including a plurality of steel plates stacked in a radial direction of impeller 10. The same effect as in the modification in FIG. 23 can be obtained in these cases as well.

Alternatively, each of yoke 19 and magnetic element 18 in FIG. 3 may be made of powders of pure iron, soft iron or ferrosilicon. In this case, iron loss in yoke 19 and magnetic element 18 can be reduced, thus increasing energy efficiency when impeller 10 is driven to rotate.

[Second Embodiment]

Figure 26:
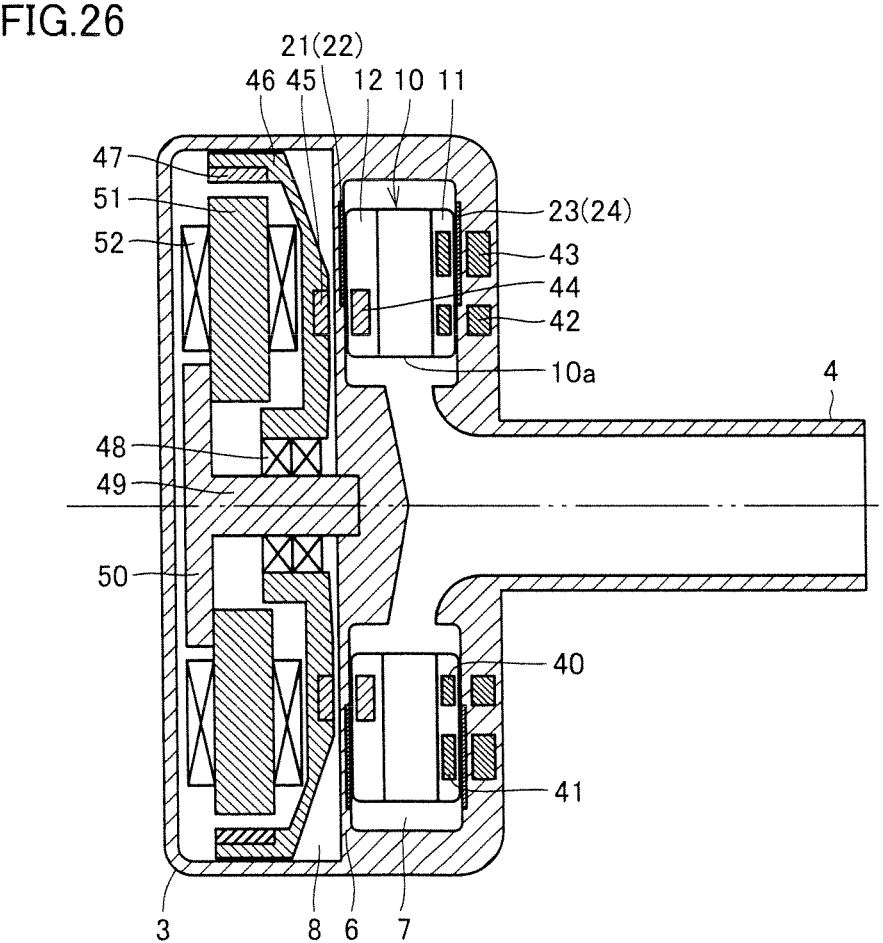
FIG. 26 is a cross-sectional view showing a structure of a pump unit of a centrifugal blood pump apparatus according to a second embodiment of the present invention.

FIG. 26 is a cross-sectional view showing a structure of a pump unit of a centrifugal blood pump apparatus according to a second embodiment of the present invention, which is compared to FIG. 3. Referring to FIG. 26, in this pump unit, permanent magnets 40, 41 are embedded in shroud 11 of impeller 10. Permanent magnet 40 is provided on a side of the rotation shaft of impeller 10 relative to permanent magnet 41. In addition, permanent magnets 42, 43 for attracting permanent magnets 40, 41, respectively, are embedded in the inner wall of blood chamber 7 facing shroud 11. Permanent magnets 40 to 43 are provided to attract (in other words, bias) impeller 10 to the side opposite to motor chamber 8, that is, toward blood inlet port 4.

Instead of providing permanent magnets 40 to 43 in shroud 11 and the inner wall of blood chamber 7, a permanent magnet may be provided in one of shroud 11 and the inner wall of blood chamber 7, and a magnetic element may be provided in the other. Alternatively, shroud 11 itself may be formed of a permanent magnet or a magnetic element. Either a soft magnetic element or a hard magnetic element may be used as the magnetic element.

A single permanent magnet 40 or a plurality of permanent magnets 40 may be provided. If a single permanent magnet 40 is provided, permanent magnet 40 is formed in a ring shape. If a plurality of permanent magnets 40 are provided, the plurality of permanent magnets 40 are arranged at regular angular intervals along the same circle. In a case of each of permanent magnets 41 to 43 as well, as with permanent magnet 40, a single permanent magnet or a plurality of permanent magnets may be provided.

A plurality of (e.g., eight) permanent magnets 44 are embedded in shroud 12. The plurality of permanent magnets 44 are arranged at regular angular intervals along the same circle. In motor chamber 8, a plurality of (e.g., eight) permanent magnets 45 for attracting the plurality of permanent magnets 44 are provided. The plurality of permanent magnets 45 are arranged at regular angular intervals along the same circle to face the plurality of permanent magnets 44 in impeller 10. The plurality of permanent magnets 44 are provided in a surface of a bowl-shaped rotor 46. A plurality of (e.g., eight) permanent magnets 47 are provided at regular angular intervals on an inner side of a circumference of rotor 46. The plurality of permanent magnets 47 are arranged at regular angular intervals along the same circle such that adjacent magnetic polarities thereof are different from each other. In other words, permanent magnet 47 having the N-pole toward the inside of rotor 46 and permanent magnet 47 having the S-pole toward the inside of rotor 46 are alternately arranged at regular angular intervals along the same circle.

A central portion of rotor 46 is rotatably supported by a central axis 49 with a bearing 48 being interposed, and rotor 46 is rotatably provided along diaphragm 6. Central axis 49 is provided to stand in a center of a disc-shaped yoke 50. A plurality of (e.g., nine) magnetic elements 51 are provided at regular angular intervals around central axis 49 on the surface of yoke 50. Tip ends of the plurality of magnetic elements 51 are arranged along the same circle, as facing the plurality of permanent magnets 47 in rotor 46. A coil 52 is wound around each magnetic element 51. The plurality of permanent magnets 47, the plurality of magnetic elements 51, and a plurality of coils 52 constitute a motor for rotating rotor 46.

Voltages are applied to nine coils 52 in a power distribution system shifted by 120 degrees, for example. Namely, nine coils 52 are divided into groups each including three coils. Voltages VU, VV and VW as shown in FIG. 8 are applied to first to third coils 52 of each group, respectively. Thus, a rotating magnetic field can be generated by applying voltages VU, VV and VW to first to third coils 52, respectively, and rotor 46 can be rotated by attractive force and repulsion force between the plurality of magnetic elements 51 and the plurality of permanent magnets 47 in rotor 46. As rotor 46 rotates, impeller 10 rotates as a result of attractive force from the plurality of permanent magnets 45 in rotor 46 and the plurality of permanent magnets 44 in impeller 10.

When impeller 10 is rotating at a rated rotation speed, attractive force between permanent magnets 40, 41 and permanent magnets 42, 43 and attractive force between the plurality of permanent magnets 44 and the plurality of permanent magnets 45 are set to be balanced with each other substantially around the center of the movable range of impeller 10 in blood chamber 7. Thus, force acting on impeller 10 due to the attractive force is very small throughout the movable range of impeller 10. Consequently, frictional resistance during relative slide between impeller 10 and housing 2 which occurs when impeller 10 is activated to rotate can be reduced. In addition, a surface of impeller 10 and a surface of the inner wall of housing 2 are not damaged (no projections and recesses in the surfaces) during the relative slide, and moreover, impeller 10 is readily levitated from housing 2 without contacting even when hydrodynamic pressure is small during low-speed rotation. Accordingly, occurrence of hemolysis/thrombus due to the relative slide between impeller 10 and housing 2 or occurrence of thrombus due to small damage (projections and recesses) to the surfaces which occurs during the relative slide can be avoided.

In addition, as in the first embodiment, a plurality of grooves for hydrodynamic bearing 21 and a plurality of grooves for hydrodynamic bearing 22 are formed in the surface of diaphragm 6 facing shroud 12 of impeller 10, and a plurality of grooves for hydrodynamic bearing 23 and a plurality of grooves for hydrodynamic bearing 24 are formed in the inner wall of blood chamber 7 facing shroud 11. When a rotation speed of impeller 10 becomes higher than a prescribed rotation speed, a hydrodynamic bearing effect is produced between each of grooves for hydrodynamic bearing 21 to 24 and impeller 10. As a result, drag is generated on impeller 10 from each of grooves for hydrodynamic bearing 21 to 24, causing impeller 10 to rotate without contacting in blood chamber 7.

Further, since both of groove for hydrodynamic bearing 23 generating high hydrodynamic pressure when a distance between impeller 10 and the inner wall of blood chamber 7 is long and groove for hydrodynamic bearing 24 generating high hydrodynamic pressure when a distance between impeller 10 and the inner wall of blood chamber 7 is short are provided, high hydrodynamic pressure can be obtained in both cases of activation for rotation and steady rotation. Therefore, impeller 10 can smoothly be activated to rotate without increasing the number of components.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

REFERENCE SIGNS LIST

1 pump unit; 2 housing; 3 body portion; 4 blood inlet port; 5 blood outlet port; 6 diaphragm; 7 blood chamber; 8 motor chamber; 10 impeller; 10a through hole; 11, 12 shroud; 13 vane; 14 blood passage; 15 to 17, 40 to 45, 47 permanent magnet; 18, 35, 37 to 39, 51 magnetic element; 19, 36, 50 yoke; 20, 52 coil; 21 to 24 groove for hydrodynamic bearing; 25 controller; 26 motor control circuit; 27, 30, 31 power amplifier; 32 switch; 46 rotor; 48 bearing; and 49 central axis.

The invention claimed is:

1. A centrifugal pump apparatus including a housing having first and second chambers partitioned from each other by a diaphragm, an impeller rotatably provided in said first chamber along said diaphragm, for delivering liquid by centrifugal force during rotation, and a drive unit provided in said second chamber for driving said impeller to rotate with said diaphragm being interposed, comprising:
   a first magnetic element provided in a first surface of said impeller;
   a second magnetic element provided in a planar surface of said first chamber facing the first surface of said impeller, for attracting said first magnetic element;
   a third magnetic element provided in a second surface of said impeller and attracted by said drive unit during rotation of said impeller, a first attractive force between said first and second magnetic elements and a second attractive force between said third magnetic element and said drive unit causing said impeller to be located substantially in a center of a movable range of said impeller in said first chamber;
   a plurality of first grooves and a plurality of second grooves, wherein:
      said plurality of first grooves and said plurality of second grooves are formed in said planar surface of said first chamber facing said first surface of said impeller;
      said plurality of first grooves alternate with and are separate from said plurality of second grooves;
      said plurality of first grooves begin at a first outer diameter and end at a first inner diameter; and
      said plurality of second grooves begin at the first outer diameter and end at the first inner diameter; and
   a plurality of third grooves and a plurality of fourth grooves, wherein:
      said plurality of third grooves and said plurality of fourth grooves are formed in a planar surface of said diaphragm facing said second surface of said impeller;
      said plurality of third grooves alternate with and are separate from said plurality of fourth grooves;
      said plurality of third grooves begin at a second outer diameter and end at a second inner diameter; and
      said plurality of fourth grooves begin at the second outer diameter and end at the second inner diameter,
   wherein at least one of a width and a depth of said plurality of second grooves is different from that of said plurality of first grooves, and at least one of a width and a depth of said plurality of fourth grooves is different from that of said plurality of third grooves.

2. The centrifugal pump apparatus according to claim 1, wherein each one of said plurality of second grooves is shallower than each one of said plurality of first grooves and each one of said plurality of fourth grooves is shallower than each one of said plurality of third grooves.

3. The centrifugal pump apparatus according to claim 2, wherein each one of said plurality of second grooves has a depth not greater than one fifth as great as a depth of each one of said plurality of first grooves and each one of said plurality of fourth grooves has a depth not greater than one fifth as great as a depth of each one of said plurality of third grooves.

4. The centrifugal pump apparatus according to claim 1, wherein each one of said plurality of second grooves is arranged between two of said plurality of first grooves and each one of said plurality of fourth grooves is arranged between two of said plurality of third grooves, and each one of said plurality of second grooves has a width not greater than two thirds as great as an interval between a corresponding two of said first grooves and each one of said plurality of fourth grooves has a width not greater than two thirds as great as an interval between a corresponding two of said plurality of third grooves.

5. The centrifugal pump apparatus according to claim 1, wherein a number of said plurality of second grooves is equal to or less than a number of said plurality of first grooves and a number of said plurality of fourth grooves is equal to or less than a number of said plurality of third grooves.

6. The centrifugal pump apparatus according to claim 5, wherein said plurality of second grooves are arranged at regular angular intervals in a direction of rotation of said impeller and said plurality of fourth grooves are arranged at regular angular intervals in the direction of rotation of said impeller.

7. The centrifugal pump apparatus according to claim 1, wherein a plurality of said third magnetic elements are provided, said plurality of third magnetic elements are arranged along a circle such that adjacent magnetic polarities are different from each other, and said drive unit includes a plurality of coils provided to face said plurality of third magnetic elements, for generating rotating magnetic field.

8. The centrifugal pump apparatus according to claim 1, wherein a plurality of said third magnetic elements are provided, said plurality of third magnetic elements are arranged along a circle such that adjacent magnetic polarities are different from each other, and said drive unit includes a plurality of fourth magnetic elements arranged to face said plurality of third magnetic elements, and a plurality of coils provided in correspondence with said plurality of fourth magnetic elements respectively and each wound around the corresponding fourth magnetic element, for generating rotating magnetic field.

9. The centrifugal pump apparatus according to claim 1, wherein said drive unit includes a rotor rotatably provided along said diaphragm in said second chamber, a fourth magnetic element provided in said rotor to face said third magnetic element, for attracting said third magnetic element, and a motor for rotating said rotor.

10. The centrifugal pump apparatus according to claim 1, wherein said liquid is blood, and said centrifugal pump apparatus is used for circulating said blood.

11. The centrifugal pump apparatus according to claim 1, wherein:
said plurality of first grooves and said plurality of second grooves curve spirally in the same direction, and/or
said plurality of third grooves and said plurality of fourth grooves curve spirally in the same direction.

* * * * *